(12) United States Patent
Vyavahare et al.

(10) Patent No.: US 11,975,109 B2
(45) Date of Patent: *May 7, 2024

(54) METHODS FOR TARGETED DELIVERY OF AGENTS TO DEGRADED ELASTIC FIBERS

(71) Applicant: CLEMSON UNIVERSITY RESEARCH FOUNDATION, Clemson, SC (US)

(72) Inventors: Naren Vyavahare, Greenville, SC (US); Aditi Sinha, Clemson, SC (US)

(73) Assignee: CLEMSON UNIVERSITY RESEARCH FOUNDATION, Clemson, SC (US)

( * ) Notice: Subject to any disclaimer, the term of this patent is extended or adjusted under 35 U.S.C. 154(b) by 512 days.

This patent is subject to a terminal disclaimer.

(21) Appl. No.: 16/876,812

(22) Filed: May 18, 2020

(65) Prior Publication Data

US 2020/0276131 A1 Sep. 3, 2020

Related U.S. Application Data

(63) Continuation of application No. 15/421,604, filed on Feb. 1, 2017, now Pat. No. 10,688,061, which is a continuation of application No. 13/929,140, filed on Jun. 27, 2013, now abandoned.

(60) Provisional application No. 61/665,431, filed on Jun. 28, 2012.

(51) Int. Cl.
| | |
|---|---|
| A61K 39/395 | (2006.01) |
| A61K 9/51 | (2006.01) |
| A61K 39/44 | (2006.01) |
| A61K 47/02 | (2006.01) |
| A61K 47/68 | (2017.01) |
| A61K 47/69 | (2017.01) |
| C07K 16/18 | (2006.01) |
| C07K 16/28 | (2006.01) |

(52) U.S. Cl.
CPC .......... *A61K 9/5146* (2013.01); *A61K 9/5153* (2013.01); *A61K 39/44* (2013.01); *A61K 47/02* (2013.01); *A61K 47/6843* (2017.08); *A61K 47/6937* (2017.08); *C07K 16/18* (2013.01); *C07K 16/2836* (2013.01)

(58) Field of Classification Search
None
See application file for complete search history.

(56) References Cited

U.S. PATENT DOCUMENTS

| | | |
|---|---|---|
| 3,918,455 A | 11/1975 | Coplan |
| 3,997,396 A | 12/1976 | Delente |
| 4,027,676 A | 6/1977 | Mattei |
| 4,801,537 A | 1/1989 | Nagarajan et al. |
| 4,806,472 A | 2/1989 | de Louvencourt et al. |
| 4,966,841 A | 10/1990 | Riley |
| 5,063,158 A | 11/1991 | Schoner et al. |
| 5,123,912 A | 6/1992 | Kaplan et al. |
| 5,162,225 A | 11/1992 | Sager et al. |
| 5,200,248 A | 4/1993 | Thompson et al. |
| 5,242,644 A | 9/1993 | Thompson et al. |
| 5,263,984 A | 11/1993 | Li et al. |
| 5,266,490 A | 11/1993 | Davis et al. |
| 5,268,229 A | 12/1993 | Phillips et al. |
| 5,432,082 A | 7/1995 | Galeotti et al. |
| 5,496,627 A | 3/1996 | Bagrodia et al. |
| 5,512,600 A | 4/1996 | Mikos et al. |
| 5,518,680 A | 5/1996 | Cima et al. |
| 5,583,023 A | 12/1996 | Cerutti et al. |
| 5,604,118 A | 2/1997 | Giri et al. |
| 5,611,981 A | 3/1997 | Phillips et al. |
| 5,716,404 A | 2/1998 | Vacanti et al. |
| 5,723,159 A | 3/1998 | Phillips et al. |
| 5,759,830 A | 6/1998 | Vacanti et al. |
| 5,770,193 A | 6/1998 | Vacanti et al. |
| 5,804,318 A | 9/1998 | Pinchuk et al. |
| 5,906,828 A | 5/1999 | Cima et al. |
| 5,942,436 A | 8/1999 | Dunn et al. |
| 5,972,505 A | 10/1999 | Phillips et al. |
| 6,303,136 B1 | 10/2001 | Li et al. |
| 6,306,424 B1 | 10/2001 | Vyakarnam et al. |
| 6,333,029 B1 | 12/2001 | Vyakarnam et al. |

(Continued)

FOREIGN PATENT DOCUMENTS

WO    WO 00/47716    8/2000

OTHER PUBLICATIONS

Anderson, et al. "Ch. 4: Host Reactions to Biomaterials and Their Evaluation" *Biomaterials Science: An Introduction to Materials in Medicine* (Ratner, et al. Ed.) Academic Press (1996) pp. 170-173.
Ausubel, et al. "Current Protocols in Molecular Biology" *John Wiley & Sons, Inc.* (2003) pp. 1-4637.
Bunge, et al. "Bridging Areas of Injury in the Spinal Cord" *Neuroscient.* 7 (2001) pp. 325-339.
Colburn, et al. "Serum anti-tropo: Anti-alpha-elastin antibody ratio assessing elastin turnover in scleroderma" *Clin. Rheum.* 11 (1992) pp. 206-210.

(Continued)

*Primary Examiner* — Yunsoo Kim
(74) *Attorney, Agent, or Firm* — DORITY & MANNING, P.A.

(57) ABSTRACT

Methods and delivery agents for treatment of connective tissue that includes elastic fibers are described. Delivery agents are nano- or micro-sized particles that include a biologically active compound useful in treatment of degraded elastic fibers, and an anchoring agent at a surface that binds at or near the area of degraded elastic fibers. The delivery agents may be utilized for targeted delivery of biologically active compounds to degraded elastic fibers so as to maintain and/or regenerate the elastin component of connective tissue, and to prevent further degradation and/or rehabilitate the structural architecture of the connective tissue.

15 Claims, 12 Drawing Sheets

(56) References Cited

U.S. PATENT DOCUMENTS

| | | |
|---|---|---|
| 6,368,859 B1 | 4/2002 | Atala |
| 6,391,538 B1 | 5/2002 | Vyavahare et al. |
| 6,468,649 B1 | 10/2002 | Zhong |
| 6,521,431 B1 | 2/2003 | Kiser et al. |
| 6,544,548 B1 | 4/2003 | Siller-Jackson et al. |
| 6,753,311 B2 | 6/2004 | Fertala et al. |
| 6,790,455 B2 | 9/2004 | Chu et al. |
| 6,858,222 B2 | 2/2005 | Nelson et al. |
| 6,861,142 B1 | 3/2005 | Wilkie et al. |
| 6,861,211 B2 | 3/2005 | Levy et al. |
| 7,056,580 B2 | 6/2006 | Dugan |
| 7,252,834 B2 | 8/2007 | Vyavahare et al. |
| 7,374,673 B2 | 5/2008 | Marcus |
| 7,479,164 B2 | 1/2009 | Girardot et al. |
| 7,713,543 B2 | 5/2010 | Vyavahare et al. |
| 7,754,243 B2 | 7/2010 | Sun |
| 7,918,899 B2 | 4/2011 | Girardot et al. |
| 8,128,952 B2 | 3/2012 | Metters et al. |
| 10,688,061 B2 * | 6/2020 | Vyavahare ............ A61K 39/44 |
| 2001/0033857 A1 | 10/2001 | Vyakarnam et al. |
| 2002/0022883 A1 | 2/2002 | Burg |
| 2003/0147966 A1 | 8/2003 | Frenzen et al. |
| 2005/0070930 A1 | 3/2005 | Kammerer |
| 2009/0214654 A1 | 8/2009 | Isenburg et al. |

OTHER PUBLICATIONS

Cole, et al. "Monoclonal Antibodies and Cancer Therapy" *Alan R. Liss, Inc.* (1985) pp. 77-96.

Conroy, et al. "Lubricious coatings for medical devices" *dds&s* 3 (2004) pp. 89-92.

Cruise, et al. "Characterization of permeability and network structure of interfacially photopolymerized poly(ethylene glycol) diacrylate hydrogels" *Biomater.* 19 (1998) pp. 1287-1294.

Goeddel, et al. "Gene Expression Technology" *Methods of Enzymology* vol. 185 Academic Press (1989).

Harlow, et al. "Antibodies, A Laboratory Manual" *Cold Spring Harbor Laboratory* (1988) pp. 1-726.

Harris, et al. "Assessment of the cytocompatibility of different coated titanium surfaces to fibroblasts and osteoblasts" *Cytocompat. Titan. Surf.* (2004) pp. 13-20.

Köhler, et al. "Continuous cultures of fused cells secreting antibody of predefined specificity" *Nature* 256 (1975) pp. 495-497.

Park, J.B. "Ch. 10: Tissue Response to Implants" *Biomaterials: An Introduction* Plenum Press (1992) pp. 230-231.

Ravid, et al. "Upregulation of lysyl oxidase in vascular smooth muscle cells by cAMP: role for adenosine receptor activation" *J. Cell. Biochem.* 75 (1999) pp. 177-185.

Sambrook, et al. "Molecular Cloning: A Laboratory Manual" 3$^{rd}$ Ed. *Cold Spring Harbor Laboratory* (2001) pp. 1-2227.

Sambrook, et al. "Molecular Cloning: A Laboratory Manual" 2$^{nd}$ Ed. *Cold Spring Harbor Laboratory* (1989) pp. 1-1626.

Sawhney, et al. "Bioerodible Hydrogels Based on Photopolymerized Poly(ethylene glycol)-co-poly(a-hydroxy acid) Diacrylate Macromers" *Macromole.* 26 (1993) pp. 581-587.

Shanley, et al. "Transforming growth factor-β1 increases lysyl oxidase enzyme activity and mRNA in rat aortic smooth muscle cells" *J. Vasc. Surg.* 25 (1997) pp. 446-452.

Silhavy, et al. "Experiments with Gene Fusions" *Cold Spring Harbor Laboratory* (1984) pp. 1-303.

Wei, et al. "Epitope Specificity of Monoclonal and Polyclonal Antibodies to Human Elastin" *Int'l. Arch. Aller. Immunol.* 115 (1998) pp. 33-41.

Homem De Bittencourt, Jr., et al. "LipoCardium: Endothelium directed cyclopentenone prostaglandin-based liposome formulation that completely reverses atherosclerotic lesions" *Atherosclerosis* 193 (2007) pp. 245-258.

Schrama, et al. "Antibody targeted drugs as cancer therapeutics" *Nat. Rev. Drug Discov.* 5 (2006) pp. 147-159.

* cited by examiner

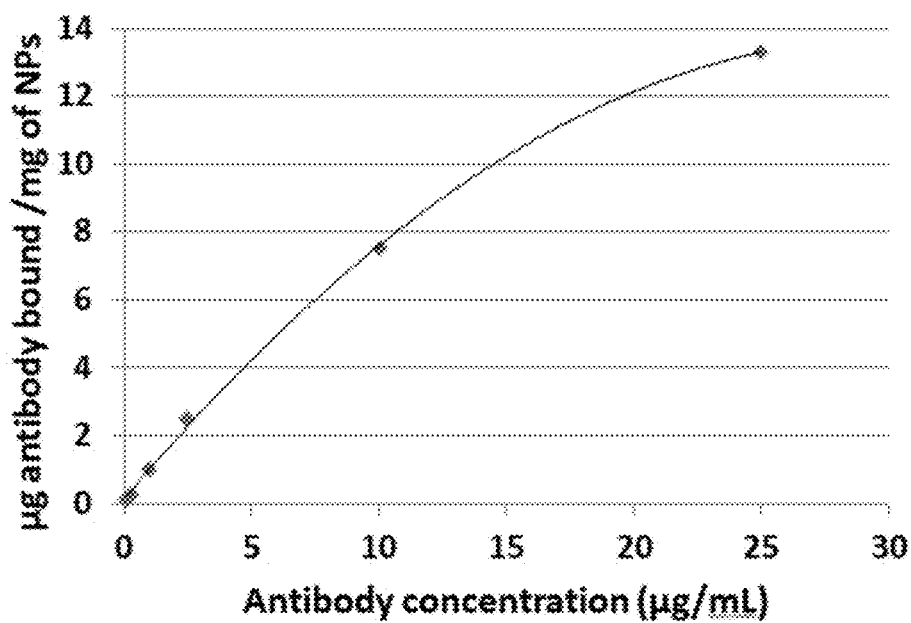
FIG. 8
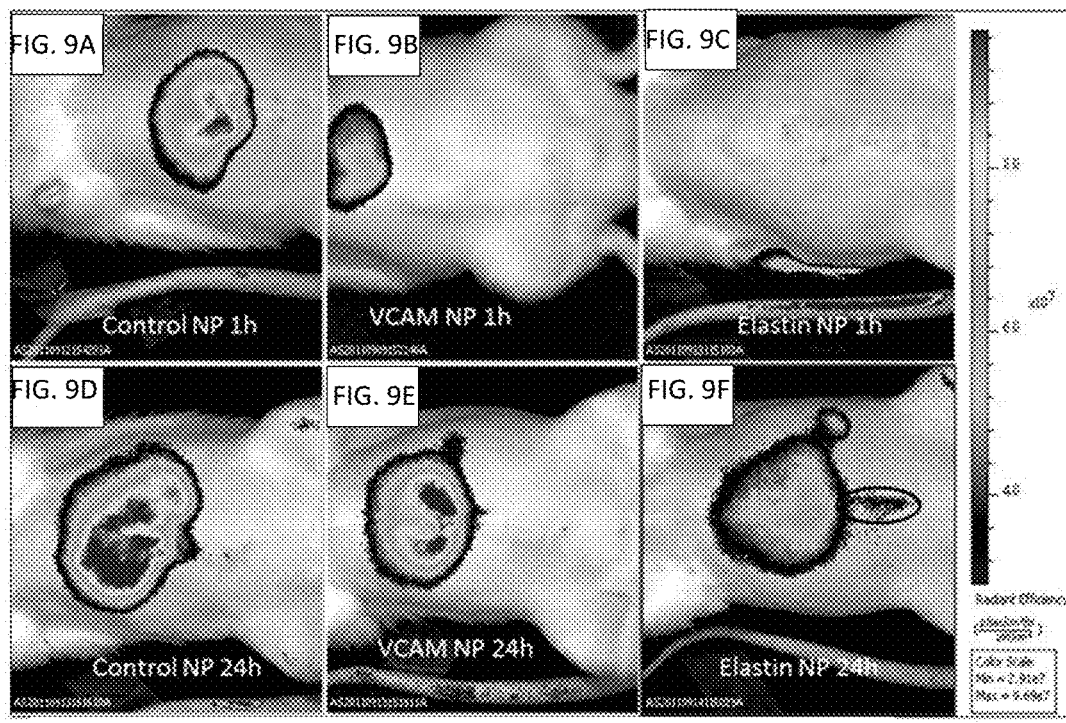

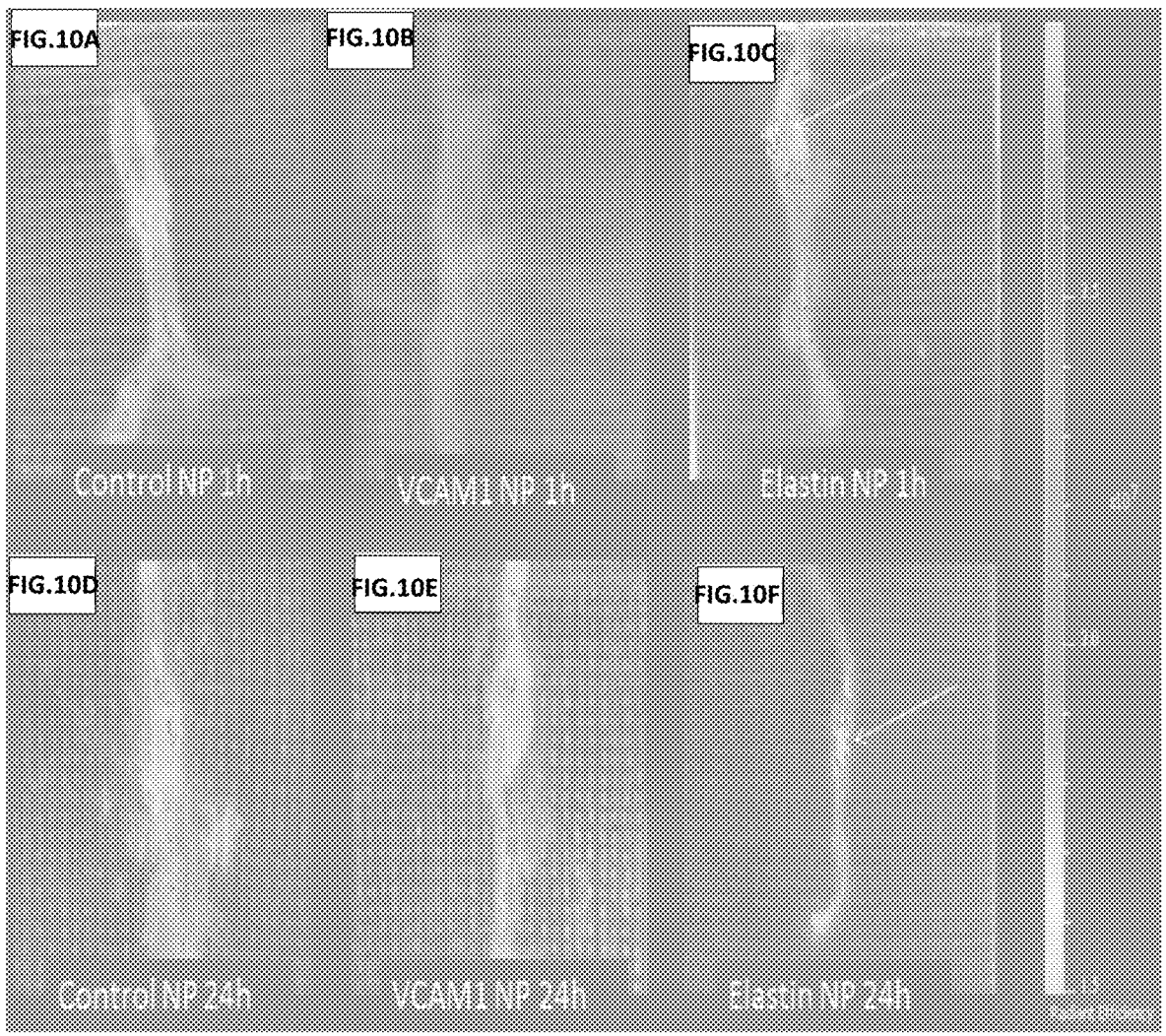

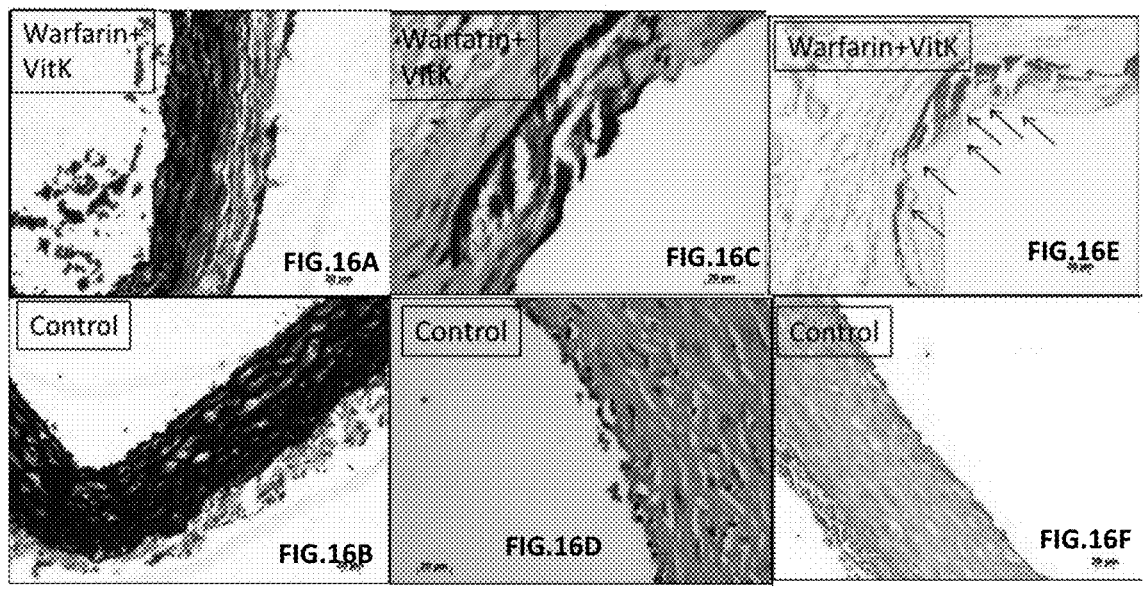
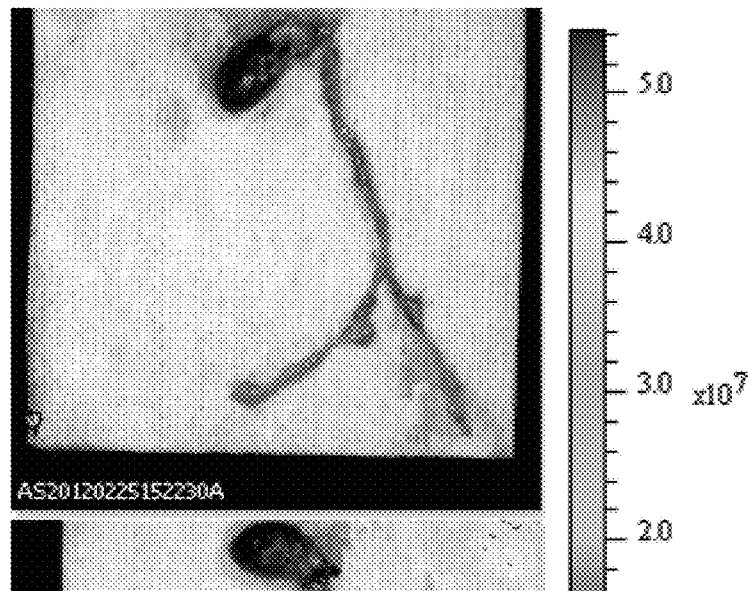
FIG. 17A
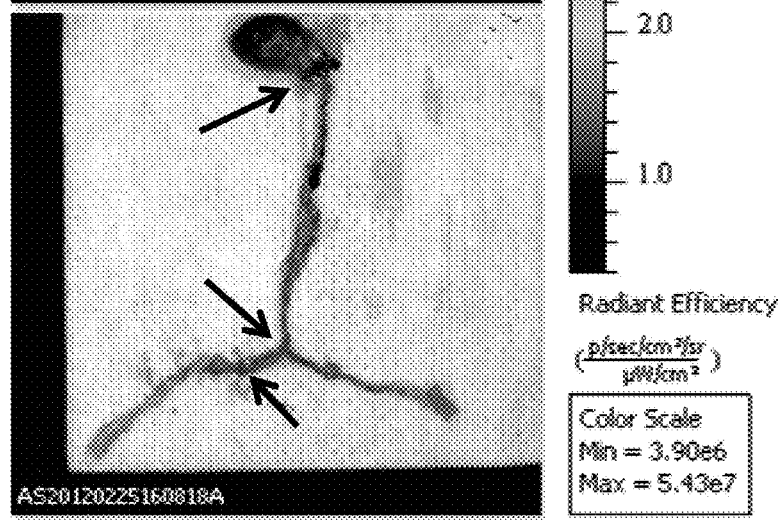
FIG. 17B

METHODS FOR TARGETED DELIVERY OF AGENTS TO DEGRADED ELASTIC FIBERS

CROSS REFERENCE TO RELATED APPLICATION

The present application is a continuation application of U.S. patent application Ser. No. 15/421,604, having a filing date of Feb. 1, 2017, which is a continuation application of U.S. patent application Ser. No. 13/929,140, having a filing date of Jun. 27, 2013, now abandoned, which claims filing benefit of U.S. Provisional Application Ser. No. 61/665,431, having a filing date of Jun. 28, 2012, all of which are incorporated herein by reference.

BACKGROUND

Connective tissue is the framework upon which other tissue, i.e., epithelial, muscle, and nervous tissues, are supported. Connective tissue generally includes individual cells not directly attached to one another and held within the extracellular matrix. The extracellular matrix, in turn, includes the ground substance (e.g., the minerals of bone, the plasma of blood, etc.) and a fibrous component including collagen fibers and elastin fibers.

Connective tissue can assume widely divergent architectures, ranging from blood, in which the fibrous component is absent and the ground substance is fluid, to dense connective tissue, which includes a relatively high proportion of extracellular fibers and may contain little of the other connective tissue components. There are many specialized types of connective tissue, one example being elastic tissue, in which elastic fibers are the major component of the tissue and the amount of factors commonly found in other types of connective tissue, such as collagen and proteoglycans, may be minimal.

Elastin is quite abundant in connective tissue and is the protein constituent of the elastic fibers found in most connective tissue. For instance, elastin is the most abundant extracellular matrix protein found in the aortic wall and is prevalent in skin and lung tissues. Elastic fibers of connective tissue are responsible for the elasticity and recoil of the tissue. Elastic fibers are formed from the microfibril peripheral scaffold and amorphous core cross-linked elastin. More specifically, amorphous elastin is formed from monomers of soluble tropoelastin that are cross-linked together to form insoluble amorphous elastin. The microfibril scaffold includes numerous proteins (e.g., glycoproteins, fibrillin, elastin receptor, etc.) and organizes and surrounds the core of amorphous elastin of the fibers. Unlike collagen, elastic fibers can uncoil into a more extended conformation when the fiber is stretched and can recoil spontaneously as soon as the stretching force is relaxed.

Elastin degradation is a common feature in much pathology including aneurysm (e.g., abdominal aortic aneurysm, brain aneurysm), chronic obstructive pulmonary disease (COPD), chronic kidney disease, hypertension, α-1 antitrypsin deficiency, Marfan's syndrome, and others, and can also occur naturally over time leading to loss of smoothness and firmness in skin as we age. Elastic fiber degradation is often caused by enzymes including elastase enzymes and matrix metalloproteinase (MMP) enzymes that can attack either or both of the elastin and the scaffolding proteins of the fiber. Such enzymes can be secreted by native cells such as vascular cells in arteries, dermal and lung fibroblasts in skin and lung, respectively, as well as by infiltrating inflammatory cells.

While many aspects of the methods and biological interactions leading to elastic fiber degradation remain unknown, many compounds have been developed or discovered that can help prevent or treat damage to tissue due to elastin degradation, such as certain polyphenolic compounds, statins, anti-inflammatory drugs, enzyme inhibitors, and the like. Unfortunately, typical delivery of such compounds is either systemic or localized delivery in which much of the compound is expected to fail to reach the target. Such delivery methods lead to the utilization of large doses of the compounds, which, in addition to adding to costs, can also cause toxic side effects to the patient. In addition, non-targeted delivery mechanisms can allow the compounds to interact with other, non-targeted structures in the body, which can alter normal function and lead to unwanted side effects.

What are needed in the art are methods and compounds that can specifically target treatment compounds to damaged elastic fibers for prevention or treatment of damage due to elastin degradation.

SUMMARY

According to one embodiment, disclosed is a delivery agent for treatment of a degraded elastic fiber. A delivery agent can include a micro- or nano-sized particle, a biologically active compound associated with the particle for treatment of the degraded elastic fiber, and an anchoring agent that is an elastin antibody or a fragment thereof attached to the surface of the particle. The anchoring agent can specifically bind the elastin of the degraded elastic fiber.

Also disclosed are methods for making the delivery agents and methods for utilizing the delivery agents. For example, the method can include incorporating the biologically active compound within the particle and attaching the elastin antibody or fragment thereof as anchoring agent to the surface of the particle.

A method for utilizing the delivery agents can include locating a delivery agent in an area that includes the degraded elastic fiber, and specifically binding the agent to elastin of the degraded elastic fiber. The biologically active compound can then be released from the particle subsequent to the binding of the anchoring agent to the elastin to treat the degraded elastic fiber.

BRIEF DESCRIPTION OF THE DRAWINGS

A full and enabling disclosure, including the best mode thereof, to one of ordinary skill in the art, is set forth more particularly in the remainder of the specification, including reference to the accompanying Figures, in which:

FIG. 8 graphically illustrates the effect of differing anchoring agent concentrations on nanoparticle binding yield.

FIGS. 9A, 9B, 9C, 9D, 9E, and 9F illustrates internal binding images of control nanoparticles (FIG. 9A), vascular cell adhesion molecule 1 (VCAM) antibody modified nanoparticles (FIG. 9B), and elastin antibody modified nanoparticles (FIG. 9C) 1 hour following injection for treatment of damaged abdominal aorta and 24 hours following injection (FIGS. 9D, 9E, and 9F, respectively).

FIGS. 10A, 10B, 10C, 10D, 10E, and 10F illustrate magnified views of the aortas of FIGS. 9A, 9B, 9C, 9D, 9E, and 9F, respectively.

FIGS. 16A, 16B, 16C, 16D, 16E, and 16F illustrate arteries of test subjects following treatment to instigate medial arterial calcification (FIG. 16A, FIG. 16C, FIG. 16E) as compared to control subjects with no treatment (FIG. 16B, FIG. 16D, FIG. 16F).

FIGS. 17A and 17B illustrate magnified views of the vascular tree for a control vasculature (FIG. 17A) and a vasculature treated with elastin antibody modified nanoparticles (FIG. 17B) following induced arterial calcification.

DETAILED DESCRIPTION

Figures 1A, 1B:
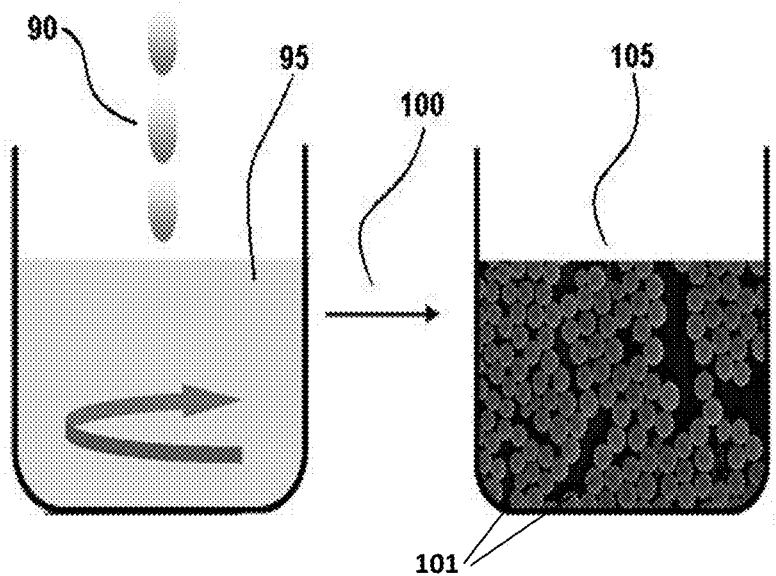
FIG. 1A and FIG. 1B illustrate one method for forming particles including an anchoring agent at a surface that specifically binds at or near an area of elastin degradation and includes FIG. 1A, in which a first solution is added dropwise to a second solution and FIG. 1B, in which particles can form in the mixture.

Reference will now be made in detail to various embodiments of the presently disclosed subject matter, one or more examples of which are set forth below. Each embodiment is provided by way of explanation, not limitation, of the subject matter. In fact, it will be apparent to those skilled in the art that various modifications and variations may be made to the present disclosure without departing from the scope or spirit of the disclosure. For instance, features illustrated or described as part of one embodiment, may be used in another embodiment to yield a still further embodiment. Thus, it is intended that the present disclosure cover such modifications and variations as come within the scope of the appended claims and their equivalents.

The present disclosure is generally directed to methods and delivery agents that may be beneficially utilized for regeneration of connective tissue, and in particular, connective tissue that includes elastic fibers. More specifically, the presently disclosed methods and delivery agents include nano- or micro-sized particles and a biologically active compound useful in treatment of degraded elastic fibers. In addition, the particles include at the surface an anchoring agent that binds at or near an area of degraded elastic fibers. The delivery agents may be utilized for targeted delivery of biologically active compounds to degraded elastic fibers so as to maintain and/or regenerate the elastin component of connective tissue, and to prevent further degradation and/or rehabilitate the structural architecture of the connective tissue. For instance, the delivery agents may be delivered directly or systemically to organs and/or structures, e.g., blood vessels, skin, lungs, etc., that incorporate connective tissue that includes the targeted degraded elastic fibers. Targeting of the delivery agents can be directed to the cross-linked amorphous elastin present in the core of the elastic fibers that becomes exposed upon degradation of the peripheral scaffolding of the elastic fibers. In one embodiment, the delivery agents and methods may be utilized in the treatment of chronic connective tissue degenerative conditions. For instance, the methods can encompass in vivo treatment methods. In particular, the disclosed delivery agents and treatment protocols are applicable to any animal or human connective tissue that includes an elastin component.

Connective tissue targeted by the process can be strengthened so as to be less susceptible to elastin degradation that can be brought about due to any of a variety of mechanisms and/or conditions including, for example, those associated with aneurysm, atherosclerotic disease, genetic susceptibilities, blunt force injury, Marfan's syndrome, COPD, pulmonary emphysema, wrinkles, pseudoxanthoma elasticum, scarring, and so forth. In one embodiment, the methods can be utilized for treatment of vascular calcification, which is common in aging, as well as in a number of genetic and metabolic disorders. Vascular calcification is now recognized as a strong predictor of cardiovascular events in those suffering from other disorders, such as in diabetic and chronic kidney disease (CKD) patients, as well as in the general population. By way of specific example, the methods can be utilized in treatment of medial arterial calcification (MAC), which can exist independently of atherosclerosis and is typically associated with elastin. Elastin-specific medial calcification leads to an elevation of systolic blood pressure (SBP) and pulse pressure (PP) and contributes to isolated systolic hypertension (ISH).

The delivery agents may have application in skin care such as for conditions including skin sagging and wrinkles, which often occur with age due to loss of elastin, or due to sun exposure or other disease states. Older patients as may benefit from utilization of the delivery agents can also include those suffering from skin arterial conditions such as cutaneous vasculitis. Cutaneous vasculitis can cause elastic lamina damage in the small arteries in the skin, and use of the delivery agents disclosed herein can alleviate such damage.

In general, any bulk biocompatible material capable of being formed to a useful size can be utilized in forming the particles of the delivery agents. In one embodiment, a polymeric particle can be utilized. For instance, particles formed from polystyrene, poly(lactic acid), polyketal, butadiene styrene, styrene-acrylic-vinyl terpolymer, poly(methyl methacrylate), poly(ethyl methacrylate), poly(alkyl cyanoacrylate), styrene-maleic anhydride copolymer, poly(vinyl acetate), poly(vinyl pyridine), poly(divinylbenzene), poly(butylene terephthalate), acrylonitrile, vinyl chloride-acrylates, poly(ethylene glycol), and the like, or an aldehyde, carboxyl, amino, hydroxyl, or hydrazide derivative thereof can be utilized. Particles formed of biological polymers such as proteins can be used in one embodiment. For instance, particles formed of albumin, dextran, gelatin, chitosan, etc. can be utilized. Such particles can be preferred in certain embodiments as they can be formed without the use of organic solvents according to known methods.

Other biocompatible materials as may be utilized in forming disclosed particles can include, without limitation, oxides such as silica, titania, zirconia, and the like, and noble metals such as gold, silver, platinum, palladium, and the like. In general, the materials will be biocompatible and nonimmunogenic.

In one embodiment, the particles can be biodegradable. For instance, biodegradable polymeric particles formed from polysaccharide and/or poly(lactic acid) homopolymers and copolymers can be used. For example, particles formed of poly(lactic-co-glycolic acid) (PLGA) copolymers and derivatives thereof can be utilized.

In one embodiment a poly(ethylene glycol) (PEG)/poly(lactic acid) (PLA) block copolymer can be utilized in forming the particles. A PEG-PLA block copolymer is an amphiphilic polymer with good stability in vivo. With good biocompatibility, the PEG hydrophilic component of the block copolymer can increase the solubility of insoluble compounds, prevent protein absorption on the particle surface, make the particles unrecognizable by the reticuloendothelial system as foreign bodies, and thereby provide particles that can have a characteristic of long circulation. Many factors may influence release of a biologically active agent from PEG-PLA block copolymer particles. The main factors including molecular weight, chain length of PEG or PLA, and PEG/PLA ratio in the polymer. The chain length of PEG and PLA can be controlled by changing the molecular weight of PEG and the concentrations of PEG and PLA. The longer the PLA chain length, the larger would be the particle size and the drug loading capability, particularly of hydrophobic drugs. As the PEG content and weight-average molecular weight (Mw) of PLA-PEG-PLA copolymers increases, the amount of drug release increases and the total molecular weight of the copolymers of the particles decreases. Drug release from particles could potentially be controlled by changing the content of PEG, molecular weight of PEG, and total molecular weight of copolymer. In case of a low molecular weight of PEG, deformation may occur due to the small molecular chain and low flexibility. The greater the molecular weight of PEG, the longer the PEG molecular chain length will be and the more stable the structure will be.

Selection of bulk nanoparticle material can be utilized to provide primary control of release rate of a biologically active compound from the loaded particle. For instance, selection of a biodegradable material can be utilized to increase the rate of compound release and provide a release mechanism that can be limited to a large extent by nanoparticle degradation rate and to a lesser extent by diffusion of the active compound from the bulk nanoparticle as. Alternatively, materials can be utilized such that active compound release rate is limited by only one of diffusion (e.g., a nondegradable particle) or nanoparticle degradation rate (e.g., essentially no diffusion of the active compound through the particle due to small matrix mesh size).

As mentioned, the particles of the delivery agents can be microparticles or nanoparticles. By way of example, the size, i.e., the average diameter of formed nanoparticles can generally be less than about 500 nanometers; for instance, less than about 200 nm, or less than about 100 nm. In one particular embodiment, the nanoparticles can be less than about 50 nm in size; for instance, about 20 nm in average diameter. In one embodiment, nanoparticles can be formed having an average diameter of between about 50 nm and about 400 nm, or between about 100 nm and about 300 nm. In one embodiment, the nanoparticles can have an average diameter of about 200 nm.

Larger particles can alternatively be formed. For instance, in other embodiments, microparticles can be formed having a size of up to about 50 micrometers (μm). In general, the preferred size of the particles can depend upon the specific application, e.g., the specific method of delivery of the agents such as via surface application (as in a cream or lotion), via parenteral injection using the respiratory or digestive tract, etc., as well as the desired release rate of a treatment compound from the particles. For instance, in one embodiment, the particles can be of a size to prevent cellular uptake so as to remain in the extracellular matrix and available for interaction with damaged elastic fibers. Thus, the particles may be larger than about 100 nm in one embodiment, as smaller particles have been shown to exhibit higher cellular uptake. Particles can also be small enough so as to penetrate endothelium and penetrate basement membrane so as to contact the elastin fibers of the connective tissue. For instance, particles can be less than about 400 nm in average diameter in one embodiment so as to penetrate endothelium and basement membrane.

Generally, the particles are substantially spherical in shape, although other shapes including, but not limited to, plates, rods, bars, irregular shapes, etc., are suitable for use. As will be appreciated by those skilled in the art, the composition, shape, size, and/or density of the particles may vary widely.

Particles can be designed with a desirable surface charge so as to better target damaged elastin. For instance, positively charged nanoparticles have shown superior cellular uptake as compared to negatively charged particles. Thus, in one embodiment, particles can be developed with a negative surface charge to maintain the particles in the extracellular matrix and avoid cellular uptake.

Disclosed particles can be loaded with one or more biologically active compounds according to any suitable method. For instance, in one exemplary embodiment illustrated in FIG. 1A and FIG. 1B, a precipitation method can be utilized to form the loaded particles in a one-step formation process. According to this method, a particle bulk material (e.g., a biocompatible polymer such as poly-(D,L-lactide-co-glycolide or a PGA/PLA copolymer) can be dissolved in a solvent to form a first solution 90. Suitable solvents can depend upon the specific materials involved. For example, organic solvents including acetone, tetrahydrofuran, dimethylsulfoxide, dimethylformamide, or acetonitrile and the like can be utilized. This first solution 90 can undergo standard processing such as sonication, etc., so as to adequately solubilize the polymer. The first solution 90 can then be added, generally dropwise, to a second solution 95 as illustrated at FIG. 1A. The second solution 95 can be, e.g., an aqueous solution. Either spontaneously or following an emulsification method, for instance following sonication, particles 101 can form that include the polymer bulk material as illustrated at FIG. 1B.

According to a single-step formation process, a biologically active compound (e.g., pentagalloylglucose (PGG)) can also be included in either the first solution 90 or the second solution 95. Upon formation of the particles 101, the biologically active compound can be incorporated in the particles with the polymer bulk material.

Biologically active compounds as may be incorporated in the particles can include any compound as may be utilized to treat degraded elastin. By way of example, biologically active compounds can include compounds that can encourage crosslinking of remaining elastin, so as to provide additional structural support to the connective tissue. Biologically active compounds can also include compounds that can upregulate elastin formation, particularly through increased formation and/or crosslinking of tropoelastin. In one embodiment, biologically active compounds as may be incorporated in a delivery agent can include inhibitors that can slow or prevent further damage to the elastic fibers of the connective tissue. Of course, a delivery agent may incorporate multiple biologically active compounds so as to present a multi-level approach to treat elastin degradation.

According to one embodiment, degradation of connective tissue may be prevented or slowed through the stabilization of the elastin component of the tissue by use of a phenolic compound that is incorporated in the delivery agent. In general, phenolic compounds as may be incorporated in a delivery agent can include a biologically active compound that includes at least one phenolic group bound to a hydrophobic core. While not wishing to be bound by any particular theory, it is believed that interaction between the phenolic compound and elastin proteins includes aspects involving both the hydroxyl group, as well as the hydrophobic core of the molecules. In particular, it is believed that phenolic compounds may stabilize elastin proteins through both steric means and bond formation and thereby protect sites on the protein susceptible to enzyme-mediated (e.g., elastase or MMP-mediated) cleavage.

It is believed that hydroxyl groups of a phenolic compound can bind elastin multivalently; for instance, via hydrogen bond formation with amino acid residues such as polar amino acid residues including methionine, glycine and proline, such that multiple proteins can interact with a single molecule to create a three-dimensional cross-link structure involving multiple elastin molecules. Moreover, in certain embodiments, the phenolic compounds can include one or more double bonds with which the phenolic compounds can covalently bind to the elastin, forming an even stronger and more permanent protective association between the phenolic compound and the elastin. In addition, the large hydrophobic regions of the elastin protein, which are believed to contain sites susceptible to elastase-mediated cleavage, are also believed to contain sites of association between the core of the phenolic compound and the protein. Thus, the association between the phenolic compound and the elastin protein molecules is believed to protect specific binding sites on the protein targeted by enzymes through the association of the protein with the hydrophobic core and can also sterically hinder the degradation of the protein through the development of the large three dimensional cross-link structures.

Phenolic compounds can include synthetic and natural phenolic compounds. For example, natural phenolic compounds can include those found in extracts from natural plant-based sources such as extracts of olive oil (e.g., hydroxytyrosol (3,4-dihydroxyphenylethanol) and oleuropein, extracts of cocoa bean that can contain epicatechin and analogous compounds, extracts of *Camellia* including *C. senensis* (green tea) and *C. assaimic*, extracts of licorice, sea whip, aloe vera, chamomile, and the like. Exemplary phenolic compounds can include, but are not limited to, flavonoids and their derivatives (e.g., anthocyanins, quercetin), flavolignans, phenolic rhizomes, flavan-3-ols including (+)-catechin and (−)-epicatechin, other tannins and derivatives thereof (such as tannic acid, pentagalloylglucose, nobotanin, epigallocatechin gallate, and gallotannins), ellagic acid, procyanidins, and the like.

In one embodiment, phenolic compounds can be tannins and derivatives thereof. Tannins can be found in many plant species and are also known as vegetable tannin. They are astringent, bitter plant polyphenolic compounds that bind to and precipitate proteins and various other organic compounds including amino acids and alkaloids. Tannins have molecular weights ranging from 500 to over 3,000 (gallic acid esters) and up to 20,000 (proanthocyanidins).

Figure 2A:
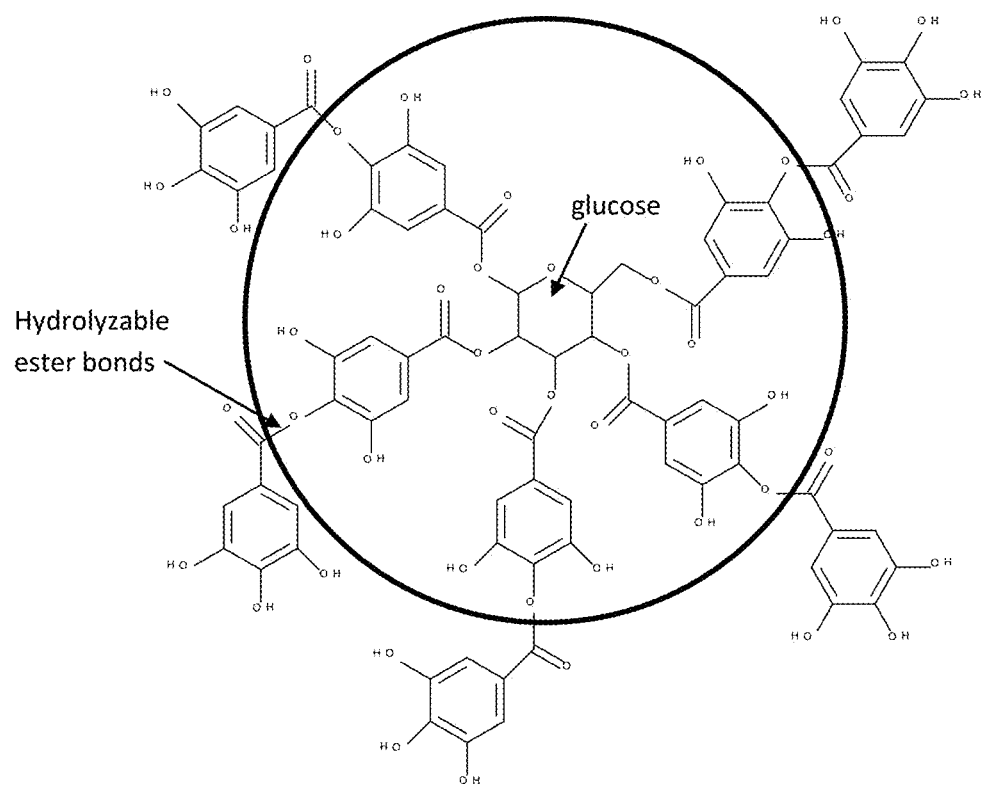
FIG. 2A is the chemical structure of a polyphenolic compound as may be utilized as the biologically active compound of a delivery agent as described herein.

Tannic acid, the structure of which is illustrated in FIG. 2, is a naturally derived tannin that may be incorporated in a delivery agent. Beneficially, tannic acid can interact with other connective tissue components, as well as elastin, and thus can stabilize additional components of the targeted connective tissue in the disclosed processes, in addition to the elastin component. For instance, tannic acid is capable of cross-linking glycosaminoglycan polysaccharides as well as other connective tissue components.

In another embodiment, the biologically active compound of the delivery agent can be pentagalloylglucose (PGG). PGG, which is the portion of a tannic acid molecule enclosed in the circle in FIG. 2A, includes the hydrophobic core of tannic acid as well as multiple phenolic hydroxyl groups, but does not possess the outer gallic acid residues and the hydrolyzable ester bonds associated with tannic acid. Thus, the possibility of release of free gallic acid residues during treatment can be prevented through utilization of a compound having no gallic acid residues, such as PGG.

Other biologically active compounds as may be utilized to treat elastin degradation may alternatively or additionally be incorporated in a delivery agent. By way of example, certain enzyme inhibitors including, without limitation, cathepsin inhibitors, MMP inhibitors, elastase inhibitors, etc., may be incorporated in the delivery agents. For instance, human cysteine cathepsins K, L, and S are known to participate in elastinolytic activity. Accordingly in one embodiment, a delivery agent can incorporate an inhibitor for cathepsins K, L, and/or S such as cystatins, which have been shown to abolish elastinolytic active of these cysteine cathepsins.

MMP inhibitors, and particularly inhibitors of MMP-2, MMP-9, and MMP-12, which have been implicated in elastin degradation, may be incorporated in a delivery agent. By way of example, one or more of the four tissue inhibitor of metalloproteinases (TIMPs), i.e., TIMP1, TIMP2, TIMP3, or TIMP4 may be included in a delivery agent. Synthetic MMP inhibitors, such as inhibitors containing a chelating group that binds the catalytic zinc atom at the MMP active site can be included in a delivery agent. Typical chelating groups include hydroxamates, carboxylates, thiols, and phosphinyls. Tetracycline antibiotics such as doxycycline, minocycline, and so forth have been shown to inhibit MMP activity. Beneficially, and due to the specific targeting capability of the delivery agents, the biologically active compounds, such as the tetracycline antibiotics, can be used in relatively small amounts, so as to prevent unwanted delivery of the agents throughout the subject's system.

Biologically active compounds can also include compounds that can encourage the formation and/or crosslinking of tropoelastin, so as to encourage formation of new elastic fibers. By way of example, as lysyl oxidase enzyme is required for elastin crosslinking, the delivery agent can incorporate lysyl oxidase directly and/or agents that increase lysyl oxidase activity such as copper ions, or forskolin, which is a cyclic AMP (cAMP) inducer. cAMP has been shown to upregulate lysyl oxidase in vascular smooth muscle cells (see, e.g., Ravid, et al., *J. Cell. Biochem.* 1999 Oct. 1; 75(1):177-85). Another compound that can be utilized to encourage crosslinking of tropoelastin is TGF-β, which has been shown to increase lysyl oxidase activity (see, e.g., Shanley, et al., *J. Vasc. Surg.* 1997 25(3); 446-52). Copper ions ($Cu^{2+}$) can enhance extracellular transport of endogenous lysyl oxidase and functional activity of endogenous and exogenous lysyl oxidase by enabling electron transfer from oxygen to facilitate oxidative deamination and aldehyde formation at lysine residues in elastin. Accordingly, a particle can incorporate copper ions; for instance, in conjunction with one or more biologically active compounds, so as to treat degraded elastic fibers. Any other compounds as are known in the art that can directly or indirectly encourage crosslinking of tropoelastin in formation of insoluble elastin; for instance, through upregulation or activity increase of lysyl oxidase, are encompassed herein.

Figure 2B:
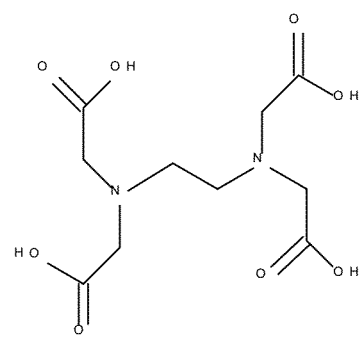
FIG. 2B is the chemical structure of a chelating agent that can be utilized as the biologically active compound of a delivery agent as described herein.

In one embodiment, an agent that can dissolve minerals, such as for example, ethylenediaminetetraacetic acid (EDTA) as illustrated in FIG. 2B, which has been shown to be a versatile chelating agent, ethylene glycol tetraacetic acid, Nitrilotriacetic acid, hydroxyethyl ethylenediaminetriacetic acid, 8-Hydroxy-7-iodo-5-quinolinesulfonic acid, poly(gamma-glutamic acid, sodium thiosulphate, alpha-lipoic acid, etc., can be incorporated in a delivery agent. Such agents can be particularly beneficial when targeting the delivery agent to calcified elastin, as is commonly found in medial arterial calcification.

Initial concentration of biologically active compound(s) within or on a particle will obviously vary depending upon the nature of the active agent, delivery rate, etc. For example, in one embodiment, loading concentration of biologically active compound in a particle can vary from about 4 wt. % to greater than about 40 wt. % by weight of the particle, with higher and lower concentrations possible depending upon specific compound, particle bulk material, and the like. For instance, in an embodiment in which a biologically active compound exhibits high solubility in the bulk particle material, a very high loading level can be attained, particularly when both materials are highly hydrophobic.

Precipitation methods such as that illustrated in FIG. 1A and FIG. 1B can be useful as such methods can provide monodisperse polymer particles loaded with a biologically active compound. Moreover, precipitation formation processes can be adjusted according to processing methods known to those skilled in the art to provide particles of a desired size and including a desired concentration of biologically active compound. For instance, modification of particle size can be obtained through modification of the concentration and/or type of surfactant included in the receiving solution 95 according to known practices.

Formation processes can include two-step processes in which particles are first formed followed by a second loading step in which one or more active agents are loaded into the formed particles. For instance, a method can include swelling a pre-formed, crosslinked polymeric particle in a solution that includes the biologically active compound so as to load the particle via a diffusion process. In another embodiment, a loading method can include double emulsion polymerization, which enables loading of hydrophilic compounds into hydrophobic particles.

Methods of forming particles loaded with a biologically active compound are not limited to the precipitation method. Other micro- and nanoparticle formation processes as are known in the art as can be utilized in forming particles loaded with active compounds. For instance, supercritical fluid processing methods as disclosed by U.S. Pat. No. 7,754,243 to Sun can be utilized to form extremely small nanoparticles, e.g., less than about 20 nm having a very narrow size distribution and little or no particles that do not include the biologically active compound in the as-formed suspension.

Loaded particles can be formed so as to control the rate of release of active compound from a particle. Suitable control mechanisms are known to those of skill in the art. For instance, release rates can depend upon the relative concentration of active compound to bulk particle material, upon the molecular weight and degradation characteristics of the bulk nanoparticle material, upon the mesh size of a polymer particle matrix, upon the binding mechanism between the surface of a particle and an active compound, and so forth, as is known. In any of these cases, one of ordinary skill in the art is capable of engineering a system so to achieve desirable release rate. For instance, in the case of purely diffusion-limited release, such control can be achieved by variation of compound concentration within particles and/or particle size, particle polymer mesh size, and so forth. In the case of purely degradation-limited release, polymer monomer units, e.g., glycolic acid content of a PLGA polymer, and/or molecular weight of particle bulk material, as well as particle size, can be adjusted to "fine tune" active compound release rate. For example, use of PLGA polymers with higher glycolic acid content and lower molecular weight can lead to an increased degradation rate of a particle formed with the polymer. Release rate of active compound from particles can be adjusted utilizing the above parameters so as to produce carriers capable of sustained release for periods varying from a few days to a few months, with the maximum release rates generally varying from a few hours to a few weeks.

According to another embodiment, release rate of an active compound can be controlled through binding, generally noncovalent binding, of the active compound to a ligand within the particle. Exemplary methods and materials of as can be utilized in one embodiment are described in U.S. Pat. No. 8,128,952 to Metters, et al., which is incorporated herein by reference. According to this method, a ligand can be selected that has an affinity for the biologically active compound to be delivered by the agent. For instance, a ligand can be selected according to a predetermined dissociation constant ($K_D$) describing this affinity and the ligand can be incorporated into the particle at a predetermined concentration level. The rate of release of the active compound from the particle that is established upon incorporation of the compound into the particle can then be controlled according to these particular parameters, i.e., $K_D$ and the concentration of the ligand.

Biologically active compounds need not necessarily be incorporated within the bulk particle material. For example, in another embodiment, a biologically active compound can be bound to the surface of a particle. For example, a compound can be bound to the surface of a particle utilizing chemistry similar to that as is described in more detail below with regard to the binding of the targeting antibodies to the particles, e.g., via glutaraldehyde crosslinking.

Delivery agents can include additional materials on or within the particles, in addition to one or more active compounds that can treat elastic fiber degradation. Such materials can be active materials, providing direct benefit to the tissue in addition to the stabilization provided by the biologically active compound, or may be supporting materials, improving delivery, compatibility, or reactivity of other materials in the delivery agent. For example, in one embodiment, the delivery agent can include glutaraldehyde. Glutaraldehyde, when targeted to connective tissue, can form covalent crosslinks between free amines in proteins in order to further stabilize the tissue.

In addition to the particle and one or more biologically active compounds, the delivery agent includes an anchoring agent that binds at or near degraded elastic fibers so as to provide the biologically active compound at the targeted site. For example, the loaded particle can be coated with an anchoring agent that can bind elastin, as degraded elastic fibers will include elastin exposed due to degradation of the microfiber scaffolding. Accordingly, in one embodiment, a delivery agent can include at a surface an antibody or a fragment thereof that is specific for elastin for targeting the agent to degraded elastic fibers and providing the biologically active compound of the delivery agent to the damaged elastic fibers at the anchoring site.

The anchoring agent bound to a surface of a particle can be a polypeptide, e.g., either a complete protein or a fragment thereof, that can recognize and bind receptors at the targeted site. This is not a requirement of the disclosed anchoring agents, however, and in another embodiment, an anchoring mechanism can utilize a non-proteinaceous anchoring agent; for instance, a polysaccharide that can bind a particle to a targeted location, e.g., elastin exposed due to degradation of the elastic fiber.

Anchoring agents, as well as biologically active compounds, can be natural or synthetic agents. For example, a proteinaceous anchoring agent (or a proteinaceous biologically active compound) can be formed using any variation of phage display protocol or the like. In one embodiment, an Affibody® fragment can be utilized. Affibody® affinity ligands are research reagents available from Abcam. They are small, simple proteins composed of a three-helix bundle based on the scaffold of one of the IgG-binding domains of Protein A, a surface protein from the bacterium *Staphylococcus aureus*. The scaffold has features as an affinity ligand and can be designed to bind with high affinity to any given target protein.

Proteinaceous anchoring agents and biologically active compounds can include polyclonal or monoclonal antibodies as desired. Antibodies can be raised according to known methods. For instance, isolated and/or purified or recombinantly produced elastin may be utilized to generate antibodies using the methods known in the art.

In one embodiment, nucleic acids encoding elastin or immunogenic epitopes thereof may be expressed and purified to obtain suitable quantity of protein that may then be utilized to generate antibodies as may be utilized as anchoring agents. For instance, recombinant expression of elastin or a targeted segment thereof may include amplifying a nucleotide sequence encoding tropoelastin from genomic DNA and then introducing the nucleotide sequence into an expression vector adapted for use in the desired expression system. The nucleotide sequence of such a construct is not limited to cDNA sequences, and the protein-encoding construct may include variations as are known to those of skill in the art including orthologs, homologs, and alleles of the cDNA encoding the protein, provided the transcribed protein product may exhibit the same or superior immunogenic response in a host as the cDNA encoded transcription products.

The nucleic acid sequence may be introduced and expressed in any host organism, for example, in either prokaryotic or eukaryotic host cells. Examples of host cells include, without limitation, bacterial cells, yeast cells, cultured insect cell lines, and cultured mammalian cells lines. Preferably, the recombinant host cell system that is selected processes and post-translationally modifies nascent peptides in a manner desired to produce the immunogenic polypeptide or protein. In one embodiment, prokaryotic organisms may be utilized, for example, *E. coli*. In other embodiments, however, a eukaryotic host may be preferred; for instance, the eukaryotic yeast *P. pastoris*.

The nucleic acid may be placed in expression cassettes for expression in the selected host. Such expression cassettes will comprise a transcriptional initiation region linked to the genetic sequence. Expression cassettes also may have a plurality of restriction sites for insertion of the nucleic acid to be under the transcriptional regulation of various control elements. The expression cassette additionally may contain selectable marker genes. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors may contain endogenous enhancers/promoters, splice junctions, intervening sequences, polyadenylation signals, etc., or a combination of both endogenous and exogenous control elements.

Generally, the nucleic acid in the vector is under the control of, and operably linked to, an appropriate promoter or other regulatory elements for transcription in a host cell. Generally, any suitable promoter may be used that is capable of operative linkage to the heterologous DNA such that transcription of the DNA may be initiated from the promoter by an RNA polymerase that may specifically recognize, bind to, and transcribe the DNA in reading frame. Moreover, while promoters may include sequences to which an RNA polymerase binds, this is not a requirement. For example, promoters of the DNA constructs may include regions to which other regulatory proteins may bind in addition to regions involved in the control of the protein translation, including coding sequences.

The vector may, if desired, be a bi-functional expression vector that may function in multiple hosts. The transcriptional cassette generally includes in the 5'-3' direction of transcription, a promoter, a transcriptional and translational initiation region, a DNA sequence of the protein, and a transcriptional and translational termination region functional in the organism. The termination region may be native with the transcriptional initiation region, may be native with the DNA sequence of the protein, or may be derived from another source.

Nucleic acids may be introduced into host cells by any method known to one of skill in the art. For example, such nucleic acids may be introduced into bacterial cells by commonly used transformation procedures such as by treatment with calcium chloride or by electroporation. If the polypeptides are to be expressed in eukaryotic host cells, nucleic acids encoding those peptides may be introduced into eukaryotic host cells by a number of means including calcium phosphate co-precipitation, spheroplast fusion, electroporation and so forth. When the eukaryotic host cell is a yeast cell, transformation may be affected by treatment of the host cells with lithium acetate or by electroporation.

A wide range of expression vectors is available in the art. Description of various expression vectors and how to use them may be found in, for example U.S. Pat. Nos. 5,604,118; 5,583,023; 5,432,082; 5,266,490; 5,063,158; 4,966,841; 4,806,472; and 4,801,537; and in Goedel et al., Gene Expression Technology, Methods of Enzymology, Vol. 185, Academic Press, San Diego (1989). Recombinant DNA and molecular cloning techniques are described by Sambrook et al., Molecular Cloning: A Laboratory Manual Vol. 1-3, Cold Spring Harbor laboratory, Cold Spring Harbor, N.Y. (2001); Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989); and by T. J. Silhavy, M. L. Berman, and L. W. Enquist, Experiments with Gene Fusions, Cold Spring Harbor Laboratory, Cold Spring Harbor, N.Y. (1984).

In accordance with one embodiment, isolated and/or purified antibodies that recognized and bind the target (e.g., elastin) may be generated. For instance, substantially pure recombinant polypeptide suitable for use as an immunogen may be isolated from cells in which it is produced and then polyclonal antiserum containing antibodies to heterogeneous epitopes of the protein may be prepared by immunizing suitable hosts with the expressed polypeptide, which may be unmodified or modified to enhance immunogenicity. Booster injections may be given at regular intervals, and antiserum harvested when antibody titer thereof, as determined semi-quantitatively, for example, by double immunodiffusion in agar against known concentrations of the antigen, begins to fall.

Another approach to raising antibodies against the target may utilize synthetic peptides synthesized on a commercially available peptide synthesizer based upon the amino acid sequence correlating to the target. Antibodies may optionally be raised against target protein by subcutaneous injection of a DNA vector that expresses the polypeptide into laboratory animals, such as mice. Delivery of the recombinant vector into the animals may be achieved according to methods as are generally known in the art.

In another embodiment, monoclonal antibodies may be raised by hybridoma cells, phage display libraries, or other methodology. Monoclonal antibodies may be e.g., human, rat, or mouse derived. For the production of human monoclonal antibodies, hybridoma cells may be prepared by fusing spleen cells from an immunized animal, e.g., a mouse, with a tumor cell. Appropriately secreting hybridoma cells may thereafter be selected according to, for example, the method of Kohler and Milstein (Nature 256: 495(1975)), or derivative methods thereof. (Procedures for monoclonal antibody production are also described in Harlow and Lane (1988). Antibodies, A Laboratory Manual, Cold Spring Harbor Laboratory, New York; Cole, et al., "Monoclonal antibodies and Cancer Therapy, Alan R. Liss, Inc., pp. 77-96.). Rodent antibodies may be humanized using recombinant DNA technology according to techniques known in the art. Alternatively, chimeric antibodies, single chain antibodies, Fab fragments, and so forth may also be developed against the polypeptides using skills known in the art.

Figure 3:
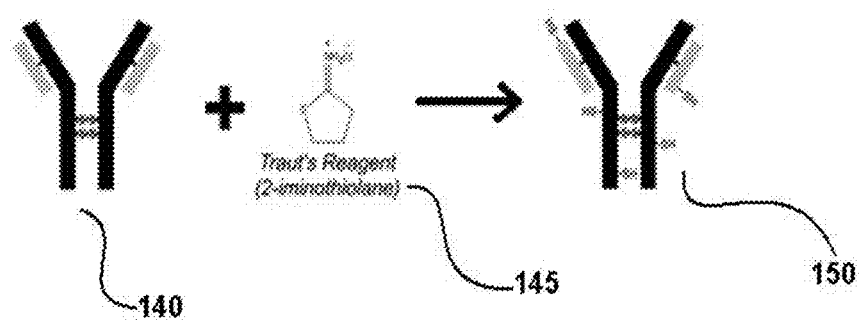
FIG. 3 illustrates one method of processing an anchoring agent for conjugation with a particle.

Following formation, the anchoring agent can be further processed so as to facilitate conjugation with the particle of the delivery agent. For example, referring to FIG. 3, one generalized schematic representation for processing the anchoring agent is illustrated. As illustrated, following initial formation of the anchoring agent, e.g., an antibody 140, the antibody 140 can be further processed so as to be more readily bound to the particle of the delivery agent. For instance, antibody 140 can be reacted with a thiolation compound 145 such as Traut's Reagent (2-iminothiolane) to produce a thiolated antibody 150.

Figure 4:
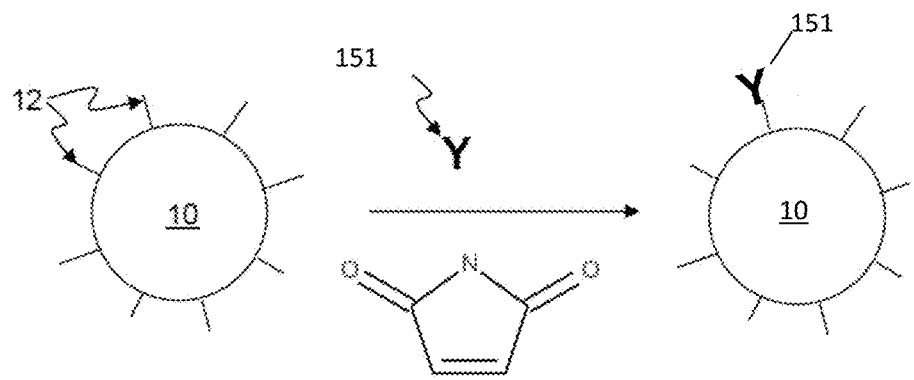
FIG. 4 illustrates one method for conjugating an anchoring agent to a particle for formation of a delivery agent.

The antibody can be conjugated with the particle according to any suitable process. For example, as illustrated in FIG. 4, a particle 10 can include surface reactive groups 12 to facilitate conjugation of the particle with an anchoring agent, e.g., an antibody 150. Surface reactive groups 12 can include, without limitation, aldehyde, +carboxyl, amino, hydroxyl, and the like. Surface reactive groups 12 can either exist on the particle surface as formed or can be added to the surface following formation, for instance via oxidation, amination, etc., of the formed particle, as is generally known in the art. The antibody can then be conjugated with the particle; for instance, through reaction with maleimide in the illustrated embodiment in which the antibody 151 is a thiolated antibody as described above.

Anchoring agents can be attached to a particle via either nonspecific adsorption or a covalent bond. Preferred attachment methods can generally depend upon the desired application of the formed conjugates. For instance, in those embodiments in which a system is designed to function in vivo, the particles can be expected to encounter multiple collisions with various biological agents and tissues. Accordingly, covalent binding can be preferred in such an embodiment, to better ensure that the anchoring agents will not be dislodged through collision of the particles with other materials.

The specific chemistry utilized to bind the anchoring agent (and optionally, the biologically active compound) to the particle surface is not particularly limited. For example, in one embodiment, a proteinaceous anchoring agent can be bound to a chloromethylated particle according to a nucleophilic substitution reaction between a protein amine group and the alkyl chloride of the particle. In another embodiment, soluble carbodiimide (EDC) and glutaraldehyde chemistry can be used to achieve covalent binding of amine groups of a proteinaceous agent to carboxylated and aminated particles, respectively. According to yet another embodiment, a proteinaceous agent can be bound to a particle through initial covalent attachment of a streptavidin monolayer to a particle followed by controllable attachment of desired amounts of biotinylated proteins. The presence of a streptavidin monolayer can also eliminate potential problems related to direct interaction of functional proteins with particles in the environment in which the particles will be utilized. According to yet another embodiment, a proteinaceous anchoring agent can be covalently attached to a particle using a crosslinking agent; for instance, a phenylazide crosslinking agent such as sulfo-HSAB (N-Hydroxysulfosuccinimidyl-4-azidobenoate) a photoreactive reagent available from Pierce, Inc. that can crosslink amine groups of the proteinaceous anchoring agent and C—H or C—C bonds of a polymeric particle.

Figure 5:
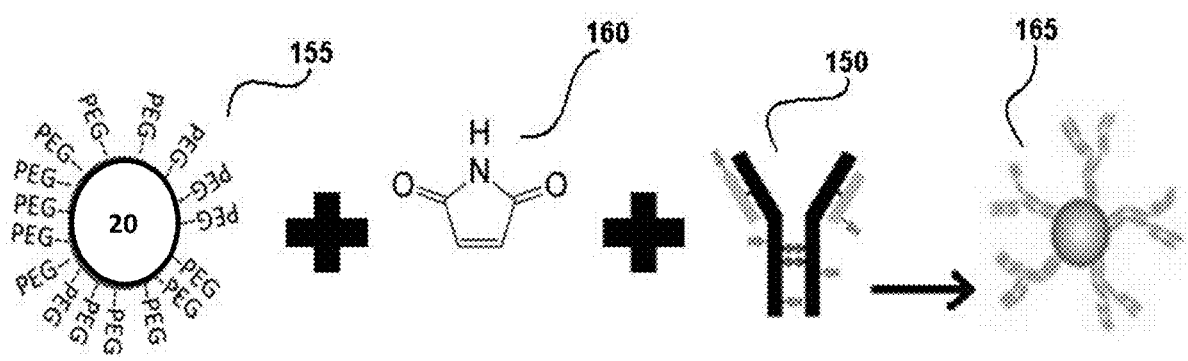
FIG. 5 illustrates another method for conjugating an anchoring agent to a particle for formation of a delivery agent.

In one embodiment, a molecular spacer, e.g., a hydrophilic spacer, can be utilized to tether an anchoring agent to a particle. Utilization of a spacer as illustrated in FIG. 5 can prevent interaction of covalently bound anchoring agents, e.g., proteins, with the particle surface and thus prevent structural changes of the protein that can lead to partial or complete loss of functionality of the protein. Spacers can include long (e.g., weight average molecular weight between about 2,000 and about 20,000 Da) hydrophilic polymers so as to minimize interaction of the bound proteins with the surface of the particle. Hydrophilic spacers can include, without limitation, poly(ethylene glycol), polyvinyl alcohol, polysaccharides, and so forth.

FIG. 5 schematically illustrates one method of attachment of a proteinaceous anchoring agent 150 to a particle 20 through a poly(ethylene glycol) (PEG) spacer 155. The PEG spacer 155 and the particle 20 can include or be processed to include functionality so as to facilitate binding to one another. For example, the PEG spacer can include aldehyde functionality and can bind to the aminated particle 20 through covalent reaction between the aldehyde group of the spacer 155 and the amine group of the particle 20. The thiolated antibody 150 can then be attached to the spacer 155 according to a simple process including mixing of a solution including the thiolated antibody 150 with an aqueous suspension of particles 20 in the presence of maleimide 160 so as to form the delivery agent 165.

At the final stage of conjugation, a particle can be blocked; for instance, with a surfactant, such as Tween® 20, Pluronic®, or dextran that can be adsorbed on the particle to block any hydrophobic surface exposed to the solution, as well as to displace any noncovalently bound agents. Low concentrations of such materials generally do not interfere with the activity of agents such as water-soluble enzymes. The presence of a surfactant can reduce undesirable protein-particle interactions and prevent particle aggregation. It can also prevent nonselective "fouling" of the surface of a particle with other proteins in the environment in which the material is utilized that could potentially deactivate a system.

As previously mentioned, surface sites of a particle to which an anchoring agent can be bound can vary. For instance, in one embodiment, carboxyl-modified particles can be utilized. For example, carboxyl-modified PLA-based particles can be utilized. According to one such embodiment, an $NH_2$-PEG-COOH spacer can be bound to a particle via the amine group using carbodiimide chemistry according to known methodology. An anchoring agent can then be likewise coupled to the carboxyl group of the spacer using carbodiimide chemistry. The surface of the particle can then be blocked with a suitable agent (e.g., Tween® 20, Pluronic®, dextran, and the like), as described above.

Beneficially, it is possible to precisely engineer a particle to exhibit anchoring properties for a desired application. For example, the binding capacity and length of time a particle can remain bound to the targeted tissue, e.g., damaged vasculature, can be engineered by altering particle size, type of the anchoring agent, and/or anchoring agent concentration on the particle surface.

According to one embodiment, a single anchoring agent can bind to more than one particle. For instance, in those embodiments in which an anchoring agent can be bound to a particle via amine groups of the protein, and as protein molecules have more than one amine group, a single protein molecule can potentially bind to more than one particle. This may result in the formation of dimers and larger aggregates of particles. While formation of large aggregates may be preferred in some embodiments; for instance, in some in vitro assay applications or in an in vivo topical application embodiment in other applications, it can be preferable to minimize aggregation. Accordingly, in one embodiment, a lower particle concentration and/or a higher concentration of surfactant, as well as variation in surfactants, can be utilized during a formation process in order to minimize aggregation of particles.

The delivery agents can be delivered to a targeting site according to any suitable method, generally depending upon where the targeting site is. For example, when considering a systemic delivery method, such as an intravenous delivery route, the delivery agents can circulate and recognize the sites of protein damage, for purposes of illustration only and not intended to be limiting, such as elastosis. Once bound to the target via the anchoring agent, the biologically active compound can be released from the particle via, e.g., particle degradation, diffusion, etc. to, e.g., prevent further enzymatic degradation of the elastin of the connective tissue.

The delivery agents may be delivered or administered acutely or chronically according to various delivery methods, including sustained release methods incorporating perivascular or endovascular patches, topical application, intravenous delivery, osmotic pumps, inhalation, and so forth.

Compositions for parenteral delivery, e.g., via injection, can include pharmaceutically acceptable aqueous and non-aqueous carriers, diluents, solvents or vehicles such as, without limitation, water, ethanol, polyols (e.g., glycerol, propylene glycol, polyethylene glycol and the like), carboxymethylcellulose and suitable mixtures thereof, vegetable oils (e.g., olive oil) and injectable organic esters such as ethyl oleate. In addition, the composition can contain minor amounts of auxiliary substances such as wetting or emulsifying agents, pH buffering agents and the like that can enhance the effectiveness of the biologically active compound. These compositions may also contain adjuvants such as preservatives, wetting agents, emulsifying agents and dispersing agents.

Prevention of the action of microorganisms may be ensured by the inclusion of various antibacterial and antifungal agents such as paraben, chlorobutanol, phenol, sorbic acid and the like. It may also be desirable to include isotonic agents such as sugars, sodium chloride and the like.

A composition can include one or more oil-soluble antioxidants including, without limitation, butylated hydroxytoluene (BHT), ascorbyl palmitate, butylated hydroxyanisole (BHA), a-tocopherol, phenyl-a-naphthylamine, hydroquinone, propyl gallate, nordihydroguaiaretic acid, and mixtures thereof, as well as any other known oil-soluble antioxidant compatible with the other components of the compositions. Mineral oils, animal oils, vegetable oils and silicones can be incorporated in a topical creams or lotions as disclosed herein. In addition to such oils, other emollients and surface active agents can be incorporated in an emulsion.

Thickeners such as natural gums and synthetic polymers, as well as preservatives such as methylparaben, butyl paraben, propylparaben and phenoxyethanol, coloring agents, and fragrances can be included in a composition; for instance, a composition for topical application such as a lotion. Other active ingredients such as sunscreen materials and antimicrobial materials may be utilized in a composition, provided, of course, that they are physically and chemically compatible with the other components of the composition.

Glycerin can be included in a formulation as a humectant; however, it can generally be present in relatively low amounts. For instance, the amount of glycerin can be less than about 10% of the total composition by weight. In one embodiment, it can be less than about 5% of the total composition by weight. It is theorized that glycerin may enhance penetration of an active ingredient, thus increasing the amount of its elastin-producing effects. Accordingly, glycerin can be present in a composition in a penetration-enhancing effective amount.

A composition may also contain, as optional additions, one or more soluble or dispersible pharmaceutically acceptable ingredients generally used in pharmaceutical emulsion compositions. Typical such ingredients include, for example, a preservative or antioxidant such as methyl or propyl paraben, butylated hydroxyanisole, imidazolidinyl urea and the like; a water or oil soluble vitamin such as vitamin C, tocopheryl linoleate and the like; and/or a colorant, odorant, humectant, thickener and the like. In general, from about 0.1 to about 15 percent total weight of such optional additives may be incorporated into a composition. Depending upon the solubility or miscibility characteristic of the particular additive, it can be incorporated into whichever emulsion phase is most suitable.

A composition may be made into a wide variety of product forms suitable for, e.g., topical administration onto the skin of a subject or internal administration to the lungs, digestive tract, or vasculature. Non-limiting examples for topical administration include a lotion, an ointment, a gel, a shampoo, a moisturizer, a sunscreen, a cream, a stick, a spray, an aerosol, foam, a paste, a mousse, and a variety of cosmetics or skin-care formulations including solid, semi-solid, or a liquid make-up such as foundations, eye make-up, etc.

Each additive of a composition may generally constitute between about 0.05% to about 15% of the total weight of the formulation. In one embodiment, a composition can include an additive in an amount between about 0.05% and about 10% or between about 0.05% and about 8%, or between about 0.05% and about 7%, or between about 0.05% and about 6%, or between about 0.05% and about 5% of the total weight of the formulation.

According to one embodiment, the delivery agents can be delivered in the form of an aerosol spray, from a pressurized pack or a nebulizer, for lung applications; for instance, in treatment of COPD, emphysema, or other lung disease in which the elasticity of the lung is affected.

Figure 6:
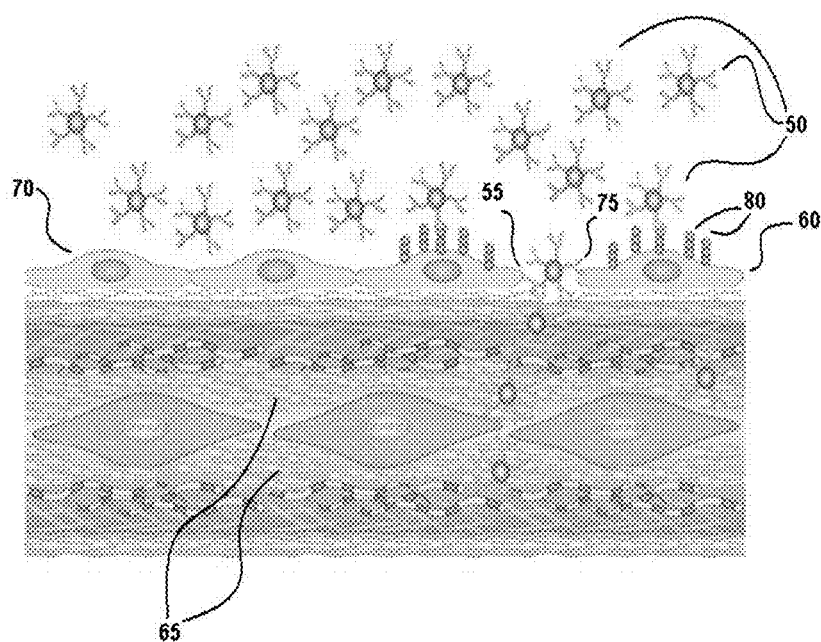
FIG. 6 schematically illustrates a method for delivery of a biologically active compound to damaged elastic fibers by use of a delivery agent as described herein.

FIG. 6 illustrates one embodiment of a proposed treatment method. Circulating delivery agents 50 can pass along a vessel wall and encounter endothelial cells. A delivery agent 50 is introduced to site 55 through damaged endothelium 60 to treat fragmented elastic fibers 65. Endothelial cells 70 show a separation in the endothelial cells at site 55. These particular endothelial cells include a higher than normal concentration of VCAM1 80 at the exposed surface. The delivery agents 50 include as an anchoring agent 75 an antibody to elastin, and delivery agents 50 that pass into the connective tissue of the vasculature via damaged site 55 can bind exposed elastin of the fragmented elastic fibers 65 within the connective tissue.

Delivery agents 50 bound at the fragmented elastic fibers 65 can then release the biologically active compound(s) of the agents so as to provide a relatively high concentration of the treatment compounds at the targeted site.

The present disclosure may be better understood with reference to the Examples, below.

Example 1

PEG/PLA nanoparticles were prepared by nano-precipitation and conjugated with either an elastin antibody, an IgG antibody, or a VCAM1 antibody.

For the preparation of nanoparticles, poly-lactic acid (PLA) and DSPE-PEG-Maleimide (4:1) were dissolved in acetone. A lipophilic near infra-red fluorescent tracer dye—1,1'-dioctadecyl-3,3,3',3'-tetramethylindotricarbocyanine iodide (DIR), was added to the polymer solution. This mixture was added dropwise to water and sonicated for 1 hour in a bath sonicator.

To conjugate the nanoparticles with an anchoring agent, rabbit anti-rat-elastin antibody, rabbit anti-rat IgG antibody, and VCAM1 antibody were thiolated using Traut's Reagent. Four µg of antibody was used for 1 mg of polymer. The thiolation was conducted for an hour at room temperature. The thiolated antibodies were separately added to the nanoparticles and left under mild shaking overnight at room temperature to form the different antibody coated nanoparticles.

Figure 7:
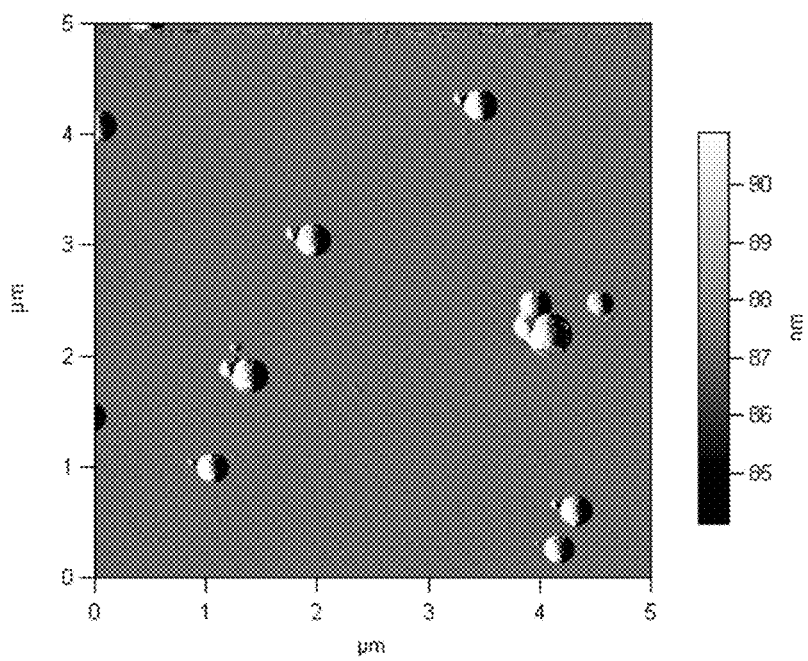
FIG. 7 is an atomic force microscopy image of delivery agents formed as described herein.

FIG. 7 is an atomic force microscope image of the as-formed nanoparticles. FIG. 8 illustrates the increasing loading level of the antibody with increasing concentration of antibody in the formation solution.

Surface charge measurements (zeta potential) were made by dissolving stock solutions as 1:100 in water in a disposable cuvette and the zeta potential was measured using the 90Plus Particle Size Analyzer (Brookhaven Instruments Co, Holtsville, N.Y.). The zeta potential was expressed in millivolts (mV) as a combined mean (±SD).

Over multiple samples, nanoparticles consistently sized approximately 200±16 nm as shown in the table below. It was observed that increasing surface density of antibodies decreased the û-potential of the nanoparticles; however; all nanoparticles had negatively charged surfaces as shown.

| Type of nanoparticle | Size (nm) | Polydispersity index | û-potential (mV) |
|---|---|---|---|
| Blank PLA | 222 | .136 | −27.91 |
| PLA + PEGmaleimide + DIR | 226 | .152 | −66 |
| NP + 0.1 µg elastin antibody | 238 | .30 | −50.69 |
| NP + 0.25 µg elastin antibody | 208 | .326 | −45.89 |
| NP + 1 µg elastin antibody | 255 | .209 | −45.91 |
| NP + 2.5 µg elastin antibody | 242 | .277 | −41.74 |
| NP + 10 µg elastin antibody | 238 | .26 | −41.93 |
| NP + 25 µg elastin antibody | 100 | .203 | −39.57 |

Example 2

Test subjects were treated to induce aneurysm. Abdominal aortic aneurysm was created in adult male Sprague Dawley rats by exposing the infra-renal abdominal aorta to 0.5M $CaCl_2$) for 15 minutes using a strip of pre-soaked sterile cotton gauze. The area was briefly rinsed with warm saline and the abdominal cavity was closed with subcutaneous suture, followed by surgical staples. The abdominal aortic aneurysm was allowed to develop for 10 days before nanoparticles formed as described above were injected through the tail vein of the rats. Control nanoparticles included no antibody modification. Antibody modified nanoparticles included elastin antibody coated nanoparticles and VCAM1 antibody coated nanoparticles.

A Caliper IVIS® Imaging System, available from Caliper LifeSciences, Hopkinton, Mass., was utilized for imaging the test subjects 1 hour and 24 hours post injection. FIGS. 9A-9C are whole body images showing test subjects injected with control nanoparticles (FIG. 9A), VCAM1 antibody modified nanoparticles (FIG. 9B), and elastin antibody modified nanoparticles (FIG. 9C) at 1 hour post injection. FIGS. 9D, 9E and 9F illustrate the same test subjects 24 hours post injection. As can be seen, the control nanoparticles gathered primarily in the liver and are relatively undispersed, while the VCAM1 antibody modified nanoparticles show some migration from the liver throughout the subject and the elastin antibody modified nanoparticles migrated to the aneurysm region. FIGS. 10A, 10B, 10C, 10D, 10E, and 10F are magnified images of the aneurysm site and further illustrate the migration of the elastin antibody modified nanoparticles to the site. Thus, while the VCAM1 antibody modified particles exhibit some specific targeting ability to the aneurysm, the elastin antibody modified nanoparticles show improved aneurysmal targeting and increased residence time as compared to both the VCAM1 antibody modified nanoparticles and the control particles.

Figure 11:
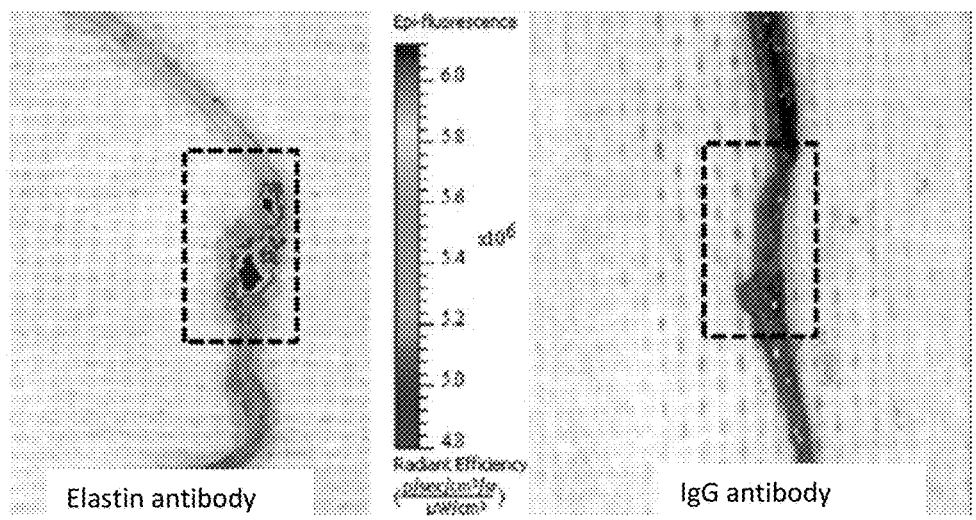
FIG. 11 illustrates images of an aorta 24 hours following intravenous injection of elastin antibody modified nanoparticles (left) and IgG antibody modified nanoparticles (right). The boxed area indicates the site of elastic fiber damage.
Figure 12:
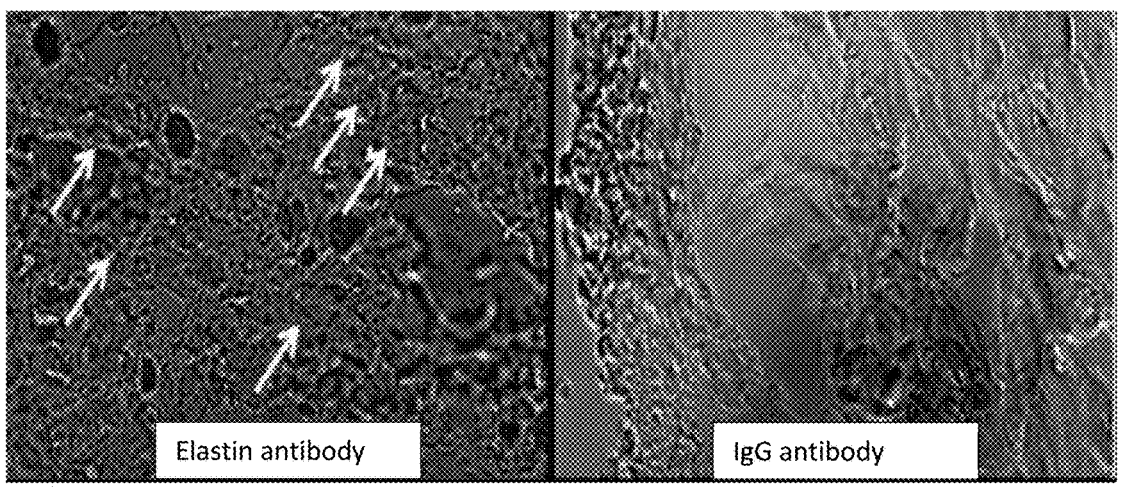
FIG. 12 are fluorescent microscopy images of damaged abdominal aortic treated with either elastin antibody modified nanoparticles (left) and IgG antibody modified nanoparticles (right). The dark coloration indicates the presence of nanoparticles in the left image.

In another sample, IgG antibody modified particles were utilized as control. The IgG antibody modified particles showed no fluorescence in the damaged area (FIG. 11). Histological assessment shown nanoparticles with surface elastin antibody were located deeply within the medial layers of the aorta, showing that they penetrated the aorta even under high shear flow conditions while no detectable fluorescence was observed in the control group (FIG. 12).

Organ distribution of nanoparticles was assessed by measuring fluorescence. At the end of 24 hours, no residual fluorescence was found in the blood, heart, brain, muscle, and skin. A biodistribution plot of the organs that exhibited fluorescence, revealed that high amount of signal was detected in the organs of mononuclear phagocytic system, namely the liver and spleen (see the table below). Splenic uptake was ~2.7 times lower in the elastin antibody modified nanoparticles than in the IgG-modified control nanoparticles, possibly because of the higher accumulation in the damaged aorta. It must be noted that rabbit anti-rat antibodies were utilized, which might be a major contributing factor to the splenic activation. Also, a small amount of fluorescent signal was observed in the kidneys probably because of the partial metabolism of low molecular weight un-encapsulated DIR molecules.

| Organ | % total fluorescence/g dry weight (IgG antibody-modified nanoparticles) | % total fluorescence/g dry weight (elastin antibody-modified nanoparticles) |
| --- | --- | --- |
| liver | 16.97 ± 1.24 | 19.09 ± 1.00 |
| aorta | 11.19 ± 5.74 | 33.19 ± 5.19 |
| lungs | 14.304 ± 2.96 | 13.37 ± 7.62 |
| kidneys | 3.58 ± 1.95 | 1.05 ± .32 |
| spleen | 175.61 ± 35.12 | 63.79 ± 13.97 |

For local nanoparticle delivery, injury to the abdominal aorta was created as described above. After 10 days, the abdominal cavity of the anesthetized subject was exposed, the injured infra-renal aorta was clamped on either end, catheterized, and particles (10 mg polymer/kg body weight) were locally perfused intra-luminally for 5 minutes (100 µl/min). Following local perfusion, blood flow in the aorta was established and animals were allowed to recover. After 24 hours, aortic sections were taken and imaged using Caliper IVIS® Lumina™ IX (Hopkinton, Mass.) with Ex/Em of 745/795.

Figure 13:
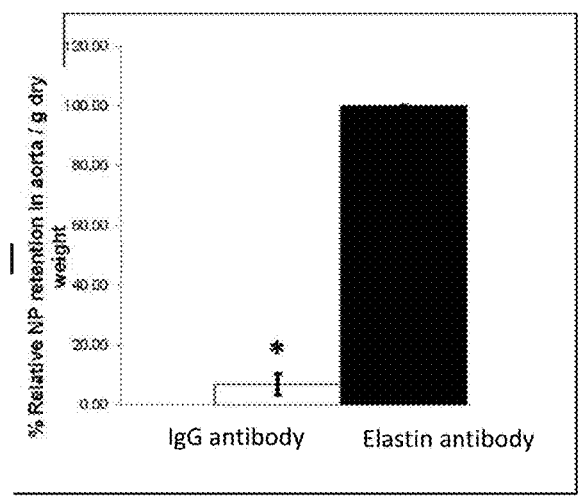
FIG. 13 illustrates the relative adherence of IgG antibody modified nanoparticles and elastin antibody modified nanoparticles 24 hours after local delivery of the nanoparticles to injured abdominal aorta.
Figure 14:
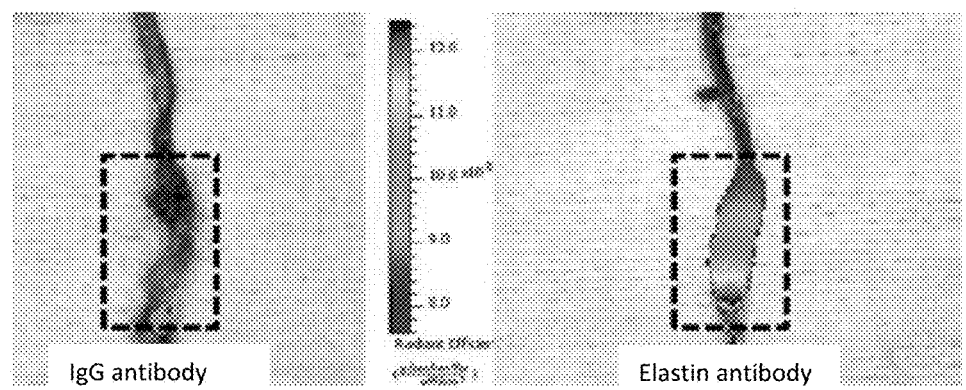
FIG. 14 illustrates IVIS imaging of the aorta 24 hours after local perfusion of IgG antibody modified nanoparticles (left) and elastin antibody modified nanoparticles (right).
Figure 15:
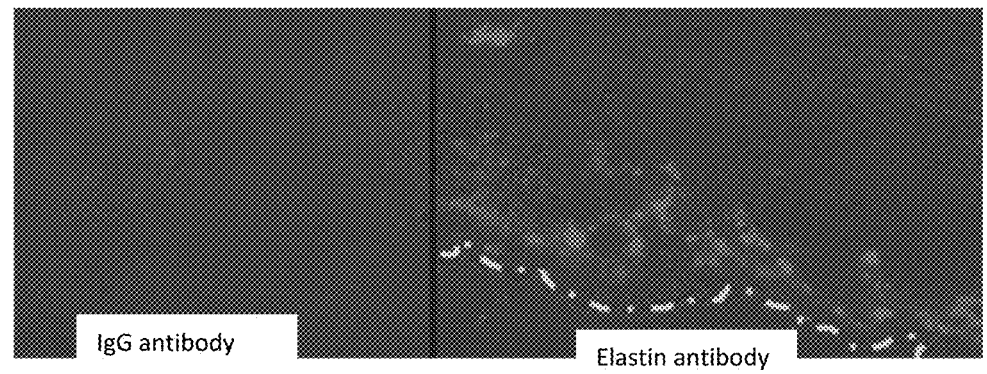
FIG. 15 illustrates fluorescent microscopy images of damaged abdominal aorta with IgG antibody modified nanoparticles (left) and elastin antibody modified nanoparticles (right) adhered. The dark spots indicate the presence of nanoparticles and dashed lanes indicate the intima of the aorta.

Twenty-four hours after injection, direct local perfusion of elastin antibody-modified nanoparticles into the site of matrix damage showed ~10-fold higher adherence and retention when compared to IgG antibody-modified control nanoparticles (FIG. 13) (elastin antibody-modified nanoparticles were assumed to display 100% attachment). The imaging of the whole aorta (FIG. 14) and histological assessment (FIG. 15) further confirmed that targeting of nanoparticles with surface elastin antibody was significantly higher than control nanoparticles and the elastin antibody-modified nanoparticles penetrated deep in the medial layers. The relative amount of elastin antibody modified nanoparticles attached to the injured area was ~43 times higher when delivered locally as compared to systemic delivery.

Example 3

Systemic arterial calcification was induced in adult Sprague Dawley rats. 6 week old male Sprague Dawley rats were given subcutaneous injections of Vitamin $K_1$ (10 mg/ml, 15 mg·kg$^{-1}$·day$^{-1}$ subcutaneous injection, every other day) and Warfarin (20 mg·kg$^{-1}$·day$^{-1}$) in drinking water. Small needles (25 G or smaller) were used and the subcutaneous injection sites were rotated between the 4 quadrants of the back to reduce stress. This routine was maintained for 3 weeks. The control group rats (n=2) were age-matched and maintained normally with no treatment. FIGS. 16A-16F illustrate the damage inflicted in the test subjects compared to the control group. Specifically, FIG. 16A (test) and FIG. 16B (control) illustrate VVG stain for elastin. The control subject (FIG. 16B) shows healthy elastin, while the test subject (FIG. 16A) shows damage in the medial arterial artery. FIG. 16C and FIG. 16D are H&E staining for a test and control, respectively, and FIG. 16E and FIG. 16F show results for alizarin red staining for calcium deposits. As can be seen, the control subject (FIG. 16F) shows homogeneous and uniform distribution while the test subject (FIG. 16E) shows distinct calcific deposits indicated by the arrows.

At the end of 3 weeks, elastin antibody modified nanoparticles formed as described above were injected through the tail vein of the rats. Following 24 hours of circulation, whole animals were euthanized and imaged using Caliper IVIS® Imaging System. Explanted aorta were rinsed with phosphate buffered saline embedded in Tissue CT compound and frozen at −80° C. 2 μm sections were cut and imaged.

FIG. 17A (control) and FIG. 17B illustrate the biodistribution and luminal targeting of the elastin antibody modified particles. The arrows of FIG. 17B are directed to large areas of fluorescence that were observed at multiple sites throughout the vascular tree of the nanoparticle treated animals. This directly correlates to the specific sites of elastin damage in the systemic model of vascular calcification and the homing of elastin antibody modified nanoparticles. No similar areas of fluorescence were seen in the control animals as illustrated in FIG. 17A. This illustrates that there is a positive relation between the area of elastin damage in the vasculature and the number of particles attaching to those particular sites. Given the heterogeneity of aneurysms and calcified sites in the vasculature, this approach is especially beneficial to deliver drugs specifically to damaged sections of the vasculature.

Example 4

High purity porcine pancreatic elastase (Elastin Products Company, Inc., Owensville, Mo.) was prepared (5 U/ml) in 100 mM Tris Buffer, 1 mM calcium chloride, 0.02% sodium azide, pH 7.8. Aortas from Sprague-Dawley rats were explanted, rinsed and treated with elastase for 10, 20, 30, and 60 minutes. The aortas were clamped on both ends and either elastin antibody-modified nanoparticles or IgG antibody-modified nanoparticles (prepared following the same method as described in Example 1) were injected intraluminally for 1 hour at room temperature. Following injection, the aortas were thoroughly washed (3 times) with PBS to minimize nonspecific adherence of nanoparticles. Simultaneously, either elastin antibody-modified nanoparticles or IgG antibody-modified nanoparticles were injected in a control aorta (without elastase treatment). Following nanoparticle infusion and washing, the aortas were lyophilized. The dry weights of the aorta were recorded. A small portion was embedded in Tissue-Tek® O.C.T.™ compound for histological analysis. The lyophilized aorta were homogenized using a PowerGen 125 Homogenizer (Fisher Scientific, MA) in Dimethyl sulfoxide (DMSO), placed in an orbital shaker for 1 hour, 37° C., 200 rpm. Tissues were centrifuged for 15 minutes at 4000×g. The supernatant was purified by filtering through 0.2 μm nylon membranes and were loaded into the HPLC for DIR quantification.

Figure 18:
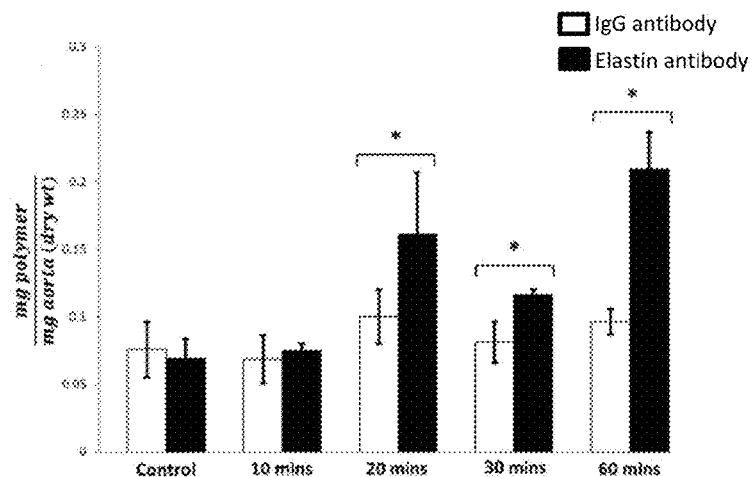
FIG. 18 illustrates rat aorta treated with elastase for various times showing nanoparticle attachment.
Figure 19:
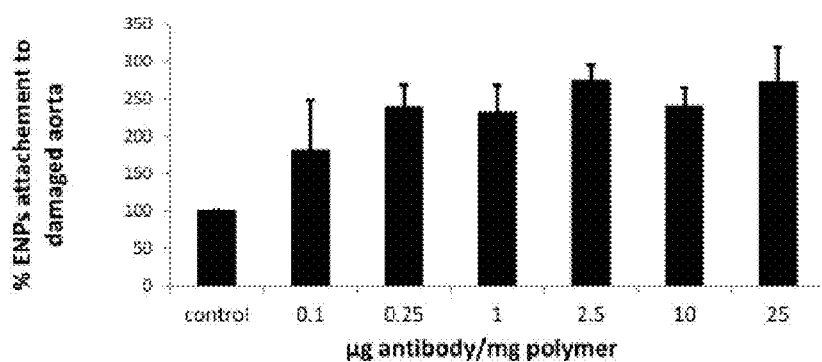
FIG. 19 illustrates increasing antibody surface density enhances target attachment efficiency up to 0.25 μg/mg polymer and stabilizes with further increase in surface antibody density.
Figure 20:
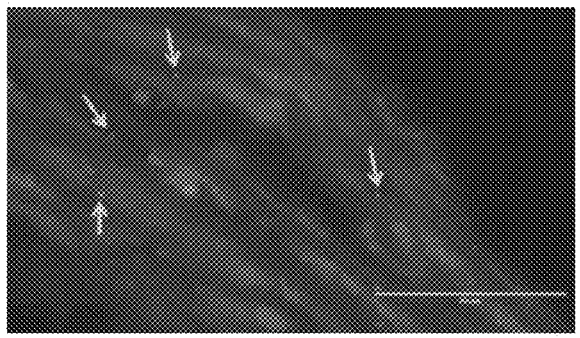
FIG. 20 illustrates elastin antibody modified nanoparticles adhered to elastase treated aorta.
Figure 21:
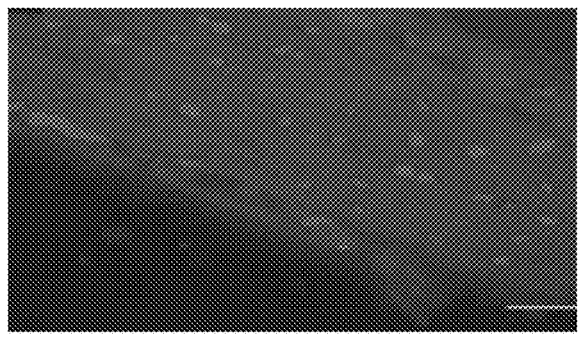
FIG. 21 illustrates IgG antibody modified nanoparticles adhered to elastase treated aorta.

On intraluminal injection of the nanoparticles, an increasing adherence of elastin antibody-modified nanoparticles with greater elastic damage was observed (FIG. 18) as assessed by quantitative fluorescence in the tissue. After 60 minutes of elastase-mediated elastic lamina degradation, there was ~2-fold greater elastin antibody-modified nanoparticle attachment in comparison with control nanoparticles. The aortas that were not treated with elastase (control groups) showed negligible adherence of any nanoparticles suggesting that elastic fiber degradation is used for nanoparticle targeting. An increase in elastin antibody-modified nanoparticle attachment efficiency was found with increase in surface antibody concentration (FIG. 19). At 2.5 μg/mg polymer a ~2.8-fold increase in attachment was recorded when compared to the control group. Further increase in surface antibody concentration did not increase attachment efficiency. Elastin antibody-modified nanoparticle uptake by the aorta was reconfirmed with histological assessment, where nanoparticles were visualized as dark dots (arrows) along the fragmented media (FIG. 20) and were evidently absent in the control INP groups (FIG. 21).

Example 5

Rat aortic vascular smooth muscle cells were treated with 2.5, 10, and 25 μg elastin antibody and 100, 500 μg/ml PLA to evaluate cytotoxicity and cellular uptake of elastin antibody modified nanoparticles. Cells were seeded at 10; 000 cells/cm$^2$. At 70% confluency, cells were incubated with nanoparticles for 4 hours following which cell viability was determined using a LIVE/DEAD™ Cell Viability Assay (Molecular Probes, Grand Island, N.Y.). Cells fluorescing green were considered alive while cells fluorescing red were considered dead. Additionally, proliferation of cells was estimated using the MTT (3-(4,5-Dimethyl-2-thiazolyl)-2, 5-diphenyl-2H-tetrazolium bromide) assay. Briefly, 5 mg of MTT (Sigma Aldrich, St. Louis, Mo.) was dissolved in 10 ml of serum-free media and added to cells. After 4 hours, media was carefully aspirated and the insoluble formazan dye was collected with dimethyl sulfoxide (DMSO) (Sigma Aldrich, St. Louis, Mo.). Absorbance was read at 560 nm and normalized to control (no treatment) readings.

To visualize the internalization of nanoparticles, nanoparticles of different sizes and surface charge were tested. Low molecular weight PLA (Average MW 9,000) was used to prepare nanoparticles by the procedure as described above, To modulate the surface charge density, purified elastin antibody modified nanoparticles were incubated with 0.2 mg poly-L-lysine/mg of polymer (Sigma Aldrich, St, Louis, Mo., Average MW 150,000-300,000) for 2 hours at room temperature.

Following incubation, the nanoparticles were thoroughly purified 2 times (centrifuged at 7000×g for 2 hours) to eliminate excess poly-L-lysine and re-suspended in water. Twenty-four hours after nanoparticle incubation, the cells were thoroughly washed with Phosphate buffered saline (PBS) to eliminate unbound nanoparticles, fixed with 4 vol. % formaldehyde, labeled with the lipophilic membrane stain Dil (Invitrogen, Carlsbad, Calif.), and then mounted with VECTASHIELD® containing the nuclear dye 40, 6-diamidino-2-phenyindole (DAPI; Vector Laboratories, Burlingame, Calif.). Imaging of cells was performed using fluorescent microscopy (EVOS® fl. Microscope, Advanced Microscopy Group, Bothell, Wash.).

Figure 22:
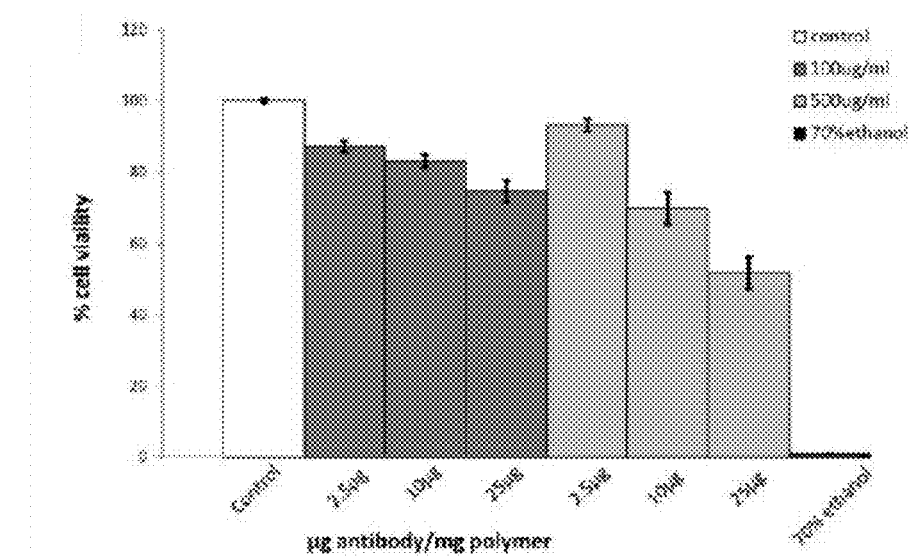
FIG. 22 illustrates the results of an MTT assay quantifying the viability of cells when treated with elastin antibody modified nanoparticles.
Figure 23:
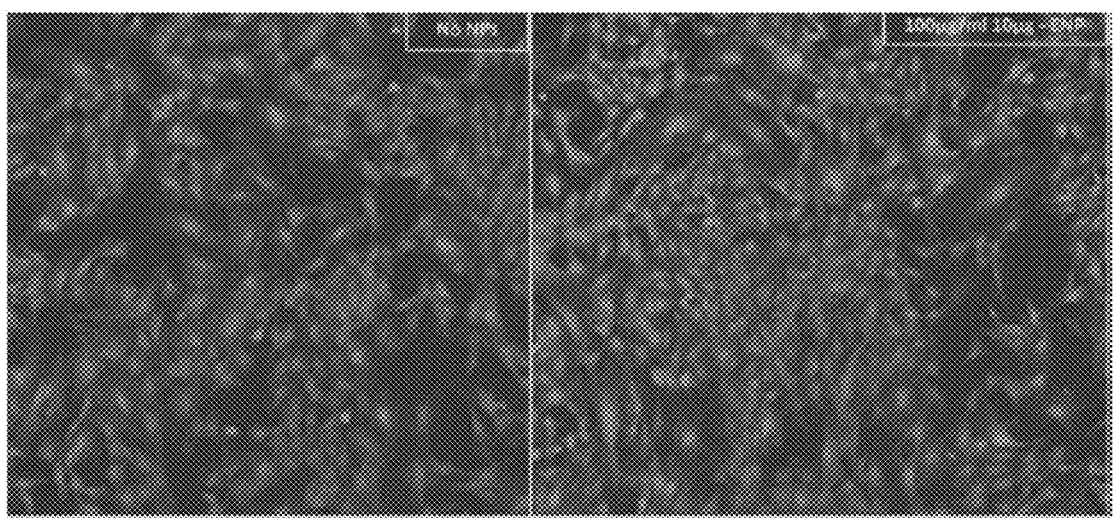
FIG. 23 illustrates the Live/Dead assay results on cells treated without (left) and with (right) elastin antibody modified nanoparticles.

MTT assay showed a significant retardation in cell proliferation when 500 μg/ml nanoparticles were placed in the cell culture media with more than 10 μg/mg levels of surface antibody concentration. Reducing the nanoparticle concentration to 100 μg/ml still led to retardation of cellular proliferation. Positive control (70% ethanol) showed more than ~95% cell death (FIG. 22). As gauged by the absence of any dead (red) cells in the LIVE/DEAD™ assay (FIG. 23), none of the groups appeared cytotoxic at any of the tested concentrations.

Figure 24:
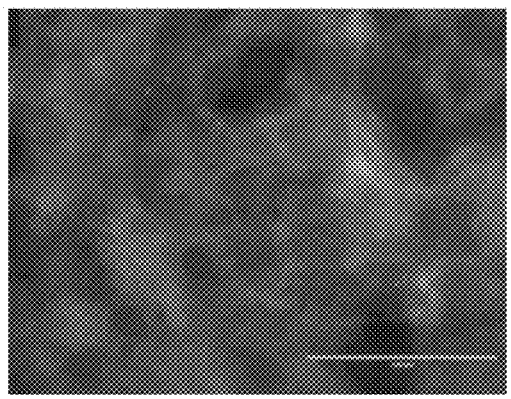
FIG. 24 illustrates the cellular exclusion of large elastin antibody modified nanoparticles.
Figure 25:
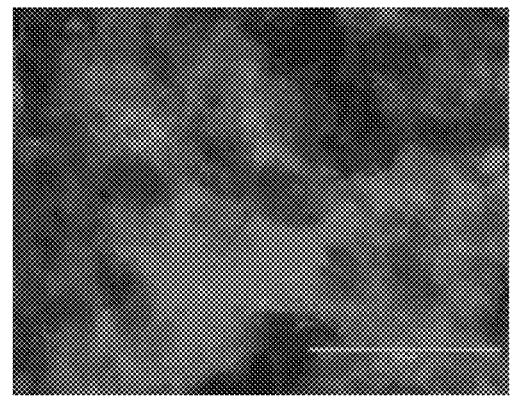
FIG. 25 illustrates the cellular uptake of small elastin antibody modified nanoparticles.
Figure 26:
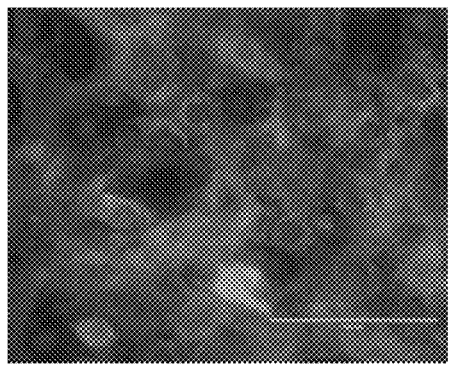
FIG. 26 illustrates the cellular uptake of small elastin antibody modified nanoparticles treated with poly-L-lysine.
Figure 27:
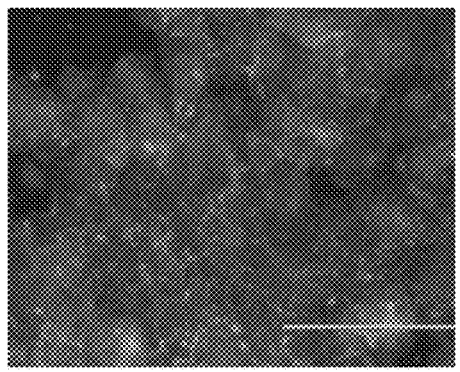
FIG. 27 illustrates the cellular uptake of large elastin antibody modified nanoparticles treated with poly-L-lysine.

The effect of particle size and charge on the intracellular uptake of DIR-loaded elastin antibody-modified nanoparticles was also examined. A majority of the particles (>200 nm) were excluded in the extracellular space at the end of 24 hours (FIG. 24), while particles below 100 nm were taken up by cells (FIG. 25). To determine the effect of surface charge on cellular uptake of the particles, elastin antibody-modified nanoparticles were incubated with poly-L-lysine to create positively charged particle surface (û-potential ~28.76 mV). When cells were presented with these positively charged particles, an enhanced cellular uptake was found, more so in smaller, positively charged elastin antibody-modified nanoparticles (FIG. 26) when compared to larger positively charged nanoparticles (FIG. 27). Overall, both size (>200 nm) and negative charge of the elastin antibody-modified nanoparticles was effective to target the nanoparticles to the extracellular matrix with minimal cellular uptake.

Example 6

Nanoparticles were prepared as described above. IgG antibody-coated nanoparticles were used for this example. The goal of the study was to determine the time required for the nanoparticles to clear out of the body after systemic injection.

Figure 28:
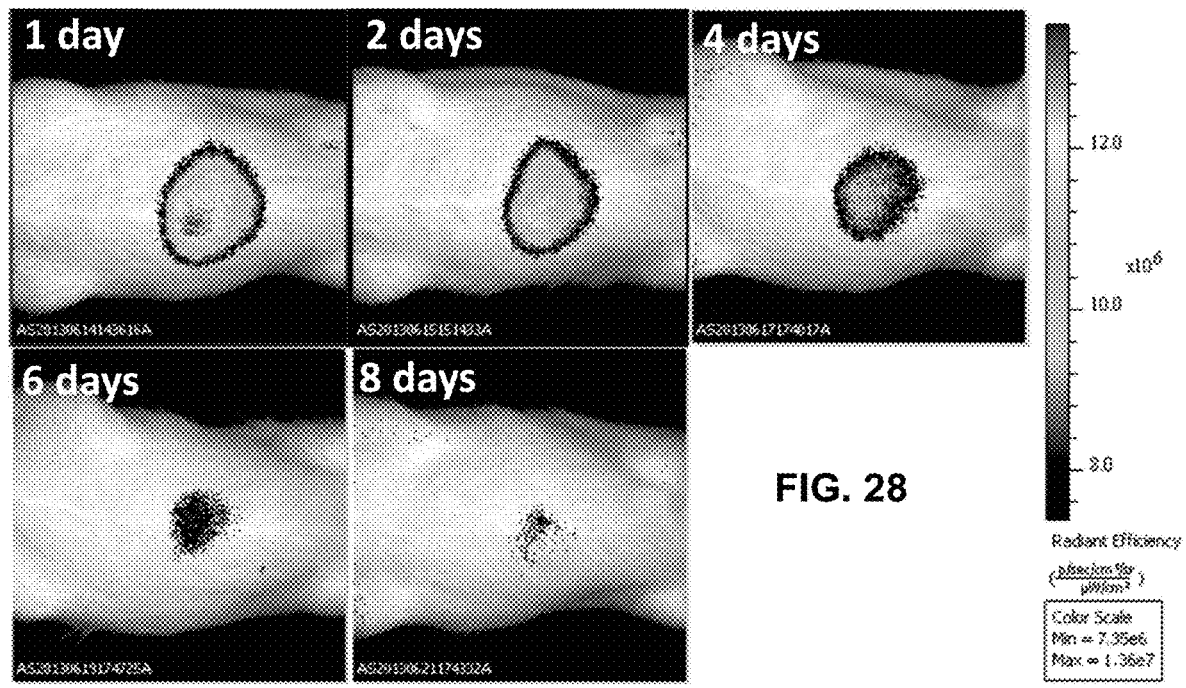
FIG. 28 illustrates the distribution and clearance of IgG antibody modified nanoparticles from a subject's body over the course of eight days.

Nanoparticles were prepared, purified and administered as described above. At various time points (1, 2, 4, 6, 8 days), the animals were anesthetized and imaged to track the distribution of nanoparticles. Results of the imaging are shown in FIG. 28. By the end of 8 days, minimal fluorescence was recorded indicating minimal retention and major clearance of nanoparticles.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations, and/or additions to the present subject matter as would be readily apparent to one of ordinary skill in the art.

What is claimed is:

1. An in vivo method for delivery of a biologically active compound to a degraded elastic fiber embedded within a live, native, damaged connective tissue of a subject, the method comprising:
   directly or systemically providing a delivery agent to the damaged connective tissue of the subject, the damage including the degraded elastic fiber, the delivery agent having an average diameter of from about 50 nm to about 400 nm and a negative surface charge, the delivery agent comprising:
   a) a biodegradable particle, the biodegradable particle comprising a biocompatible polymer, the biodegradable particle being associated with the biologically active compound, the biologically active compound comprising a tannin, a flavonoid, a flavolignan, a phenolic rhizome, a favan-3-ol a cathepsins inhibitor, an MMP inhibitor, an elastase inhibitor, a lysyl oxidase, copper ions, forskolin, TGF-β, ethylenediaminetetraacetic acid (EDTA), ethylene glycol tetraacetic acid, Nitrilotriacetic acid, hydroxyethyl ethylenediaminetriacetic acid, 8-Hydroxy-7-iodo-5-quinolinesulfonic acid, poly(gamma-glutamic acid), sodium thiosulphate, or alpha-lipoic acid,
   b) a molecular spacer bonded to a surface of the biodegradable particle at a first end of the molecular spacer, and
   c) an anti-elastin antibody or an elastin binding fragment thereof that has been modified to include thiol functionality, wherein the thiolated anti-elastin antibody or thiolated elastin binding fragment thereof is bonded to a second end of the molecular spacer via the thiol functionality and is present on the delivery agent at a concentration of from 1 microgram anti-elastin antibody or elastin binding fragment thereof per milligram delivery agent to 7.5 microgram anti-elastin antibody or elastin binding fragment thereof per milligram delivery agent; wherein
   following the step of providing the delivery agent to the subject, the delivery agent migrates to the damaged connective tissue and penetrates a medial layer of the damaged connective tissue, whereupon the anti-elastin antibody or elastin binding fragment thereof binds exposed elastin of the degraded elastic fiber and thereby binds the particle to the degraded elastic fiber embedded within the live, native, damaged connective tissue of the subject.

2. The method of claim 1, the biologically active compound being released from the biodegradable particle subsequent to the binding of the biodegradable particle to the degraded elastic fiber.

3. The method of claim 2, wherein the biologically active compound is released from the biodegradable particle via degradation of the biodegradable particle.

4. The method of claim 2, wherein the biologically active compound is released from the biodegradable particle via diffusion from the biodegradable particle.

5. The method of claim 1, wherein the subject has been diagnosed with aneurysm, atherosclerotic disease, genetic susceptibilities, blunt force injury, Marfan's syndrome, COPD, pulmonary emphysema, wrinkles, pseudoxanthoma elasticum, scarring, or vascular calcification.

6. The method of claim 1, wherein the delivery agent is provided to the subject via parenteral delivery, topical delivery, intravenous delivery, or aerosol spray delivery.

7. The method of claim 1, wherein the thiolated anti-elastin antibody or thiolated elastin binding fragment thereof is bonded to more than one biodegradable particle.

8. The method of claim 1, wherein the delivery agent has an average diameter of from about 100 nm to about 300 nm.

9. The method of claim 1, the biocompatible polymer comprising a homopolymer or copolymer comprising polysaccharide, a poly(lactic acid), or a poly(ethylene glycol).

10. The method of claim 9, the biocompatible polymer comprising a copolymer comprising poly(lactic acid) and poly(ethylene glycol).

11. The method of claim 1, the biologically active agent comprising a tannin.

12. The method of claim 11, the biologically active agent comprising pentagalloylglucose.

13. The method of claim 1, the molecular spacer comprising a poly(ethylene glycol).

14. The method of claim 1, the molecular spacer having a weight average molecular weight of between about 2,000 Da and about 20,000 Da.

15. The method of claim 1, wherein the live, native, damaged connective tissue comprises damaged vasculature of the subject.

* * * * *